US010786613B2

(12) United States Patent
Pouchoulin et al.

(10) Patent No.: US 10,786,613 B2
(45) Date of Patent: Sep. 29, 2020

(54) APPARATUS AND METHOD FOR DETERMINING A PARAMETER INDICATIVE OF THE PROGRESS OF AN EXTRACORPOREAL BLOOD TREATMENT

(71) Applicant: GAMBRO LUNDIA AB, Lund (SE)

(72) Inventors: Dominique Pouchoulin, Tramoyes (FR); Bernard Bene, Irigny (FR)

(73) Assignee: Gambro Lundia AB, Lund (SE)

( * ) Notice: Subject to any disclaimer, the term of this patent is extended or adjusted under 35 U.S.C. 154(b) by 134 days.

(21) Appl. No.: 16/092,715

(22) PCT Filed: Apr. 14, 2017

(86) PCT No.: PCT/EP2017/059062
§ 371 (c)(1),
(2) Date: Oct. 10, 2018

(87) PCT Pub. No.: WO2017/186521
PCT Pub. Date: Nov. 2, 2017

(65) Prior Publication Data
US 2019/0134290 A1     May 9, 2019

(30) Foreign Application Priority Data

Apr. 26, 2016    (EP) .................................... 16166990

(51) Int. Cl.
*A01M 1/16*    (2006.01)
*A01M 1/10*    (2006.01)
(Continued)

(52) U.S. Cl.
CPC ........ *A61M 1/1609* (2014.02); *A61M 1/1039* (2014.02); *A61M 2205/33* (2013.01);
(Continued)

(58) Field of Classification Search
CPC .............. A61M 1/1039; A61M 1/1609; A61M 2205/33; A61M 2205/3327; A61M 2205/3334; A61M 2205/52
See application file for complete search history.

(56) References Cited

U.S. PATENT DOCUMENTS 5,100,554 A    5/1992  Polaschegg
5,310,469 A    5/1994  Cunningham et al.
(Continued)

FOREIGN PATENT DOCUMENTS

CA    2863264     9/2007
EP    0547025     6/1993
(Continued)

OTHER PUBLICATIONS

European Search Report—Appl. No. 16166990.8-1651 dated Oct. 13, 2016—7 pages.
(Continued)

*Primary Examiner* — Dirk R Bass
(74) *Attorney, Agent, or Firm* — K&L Gates LLP

(57) ABSTRACT

An apparatus and process for extracorporeal treatment of blood (1) comprising a treatment unit (2), a blood withdrawal line (6), a blood return line (7), a preparation line (19) and a spent dialysate line (13). A control unit (10) is configured to calculate values of a parameter relating to treatment effectiveness based on measures of lactate or citrate or acetate concentration in the spent dialysate line (13).

20 Claims, 5 Drawing Sheets

(51) Int. Cl.
*A61M 1/16* (2006.01)
*A61M 1/10* (2006.01)

(52) U.S. Cl.
CPC .............. *A61M 2205/3327* (2013.01); *A61M 2205/3334* (2013.01); *A61M 2205/52* (2013.01)

(56) References Cited

U.S. PATENT DOCUMENTS

| | | |
|---|---|---|
| 5,567,320 A | 10/1996 | Goux et al. |
| 6,110,384 A | 8/2000 | Goux et al. |
| 6,187,199 B1 | 2/2001 | Goldau |
| 2001/0004523 A1 | 6/2001 | Bosetto et al. |
| 2003/0216677 A1 | 11/2003 | Pan et al. |
| 2014/0190885 A1 | 7/2014 | Meyer et al. |
| 2014/0190886 A1 | 7/2014 | Pudil et al. |
| 2014/0319030 A1 | 10/2014 | Shah et al. |

FOREIGN PATENT DOCUMENTS

| | | |
|---|---|---|
| EP | 0658352 | 6/1995 |
| EP | 0920877 | 6/1999 |
| EP | 0986410 | 3/2000 |
| EP | 1950568 | 7/2008 |
| EP | 2687248 | 1/2014 |
| WO | 9918979 | 4/1999 |
| WO | 9944982 | 9/1999 |
| WO | 2007101064 | 9/2007 |
| WO | 2009016504 | 2/2009 |
| WO | 2011037702 | 3/2011 |
| WO | 2012127513 | 9/2012 |
| WO | 2012171030 | 12/2012 |
| WO | 2014121162 | 8/2014 |
| WO | 20160188950 | 12/2016 |

OTHER PUBLICATIONS

International Search Report—Appl. No. PCT/EP2017/059062 dated Jul. 10, 2017—6 pages.
Written Opinion of the International Searching Authority—Appl. No. PCT/EP2017/059062 dated Jul. 10, 2017—8 pages.

APPARATUS AND METHOD FOR DETERMINING A PARAMETER INDICATIVE OF THE PROGRESS OF AN EXTRACORPOREAL BLOOD TREATMENT

PRIORITY CLAIM

The present application is a National Phase of International Application No. PCT/EP2017/059062, filed Apr. 14, 2017, which claims priority to European Patent Application No. 16166990.8, filed Apr. 26, 2016, the entire contents of each of which are incorporated herein by reference and relied upon.

The invention relates to an apparatus and to a method for determining a parameter indicative of the progress of an extracorporeal blood treatment, in particular a purification treatment whose purpose is to alleviate renal insufficiency, such as hemodialysis or hemodiafiltration.

In a hemodialysis treatment a patient's blood and a treatment liquid approximately isotonic with blood are circulated in a respective compartment of hemodialyzer, so that, impurities and undesired substances present in the blood (urea, creatinine, etc.) may migrate by diffusive transfer from the blood into the treatment liquid. The ion concentration of the treatment liquid is chosen such as to correct the ions concentration of the patient's blood.

In a treatment by hemodiafiltration, a convective transfer by ultrafiltration, resulting from a positive pressure difference created between the blood side and the treatment-liquid side of the membrane, is added to the diffusive transfer obtained by dialysis.

It is of interest to be able to determine, throughout a treatment session, one or more parameters indicative of the progress of the treatment so as to be able, where appropriate, to modify the treatment conditions that were initially fixed or to at least inform the patient and the medical personnel about the effectiveness of the treatment.

The knowledge of one or more of the following parameters may make it possible to follow the progress of the treatment, and for instance may allow to assess the suitability of the initially fixed treatment conditions:
  the actual dialysance D or the actual clearance K of the exchanger for a given solute (the dialysance D and the clearance K representing the purification performance of the exchanger),
  the dialysis dose administered after a treatment time t, which, according to the work of Sargent and Gotch, may be linked to the dimensionless ratio KT/V, where K is the actual clearance in the case of urea, T the elapsed treatment time and V the volume of distribution of urea, i.e. the total volume of water in the patient (Gotch F. A. and Sargent S. A., "A mechanistic analysis of the National Cooperative Dialysis Study (NCDS)", Kidney Int. 1985, Vol. 28, pp. 526-34).

The determination of these parameters requires precise knowledge of a physical or chemical characteristic of the blood. As it can be understood, determination of this characteristic cannot in practice be obtained by direct measurement on a specimen for therapeutic, prophylactic and financial reasons. Indeed, it is out of the question taking multiple specimens necessary to monitor the effectiveness of the treatment from a patient who is often anemic; furthermore, given the risks associated with handling specimens of blood which may possibly be contaminated, the general tendency is to avoid such handling operations; finally, laboratory analysis of a specimen of blood is both expensive and relatively lengthy, this being incompatible with the desired objective of knowing the effectiveness of a treatment while the treatment is still ongoing. Several methods have been proposed for in vivo determining hemodialysis parameters without having to take measurements on blood samples.

Document EP 0547025 describes a method for determining the concentration of a substance, such as sodium, in a patient's blood subjected to a hemodialysis treatment. This method also makes it possible to determine the dialysance D—for example for sodium—of the hemodialyzer used. The method comprises the steps of circulating a first and a second hemodialysis liquids having different sodium concentrations in succession through the hemodialyzer, measuring the conductivity of the first and second dialysis liquids upstream and downstream of the hemodialyzer, and computing the concentration of sodium in the patient's blood (or the dialysance D of the hemodialyzer for sodium) from the values of the conductivity of the liquid which are measured in the first and second dialysis liquids upstream and downstream of the hemodialyzer. Document EP 0658352 describes another method for the in vivo determination of hemodialysis parameters, which comprises the steps of: making at least a first and a second treatment liquids, having a characteristic (the conductivity, for example) associated with at least one of the parameters (the ion concentration of the blood, the dialysance D, the clearance K, KT/V, for example) indicative of the treatment, flow in succession through the hemodialyzer, the value of the characteristic in the first liquid upstream of the exchanger being different from the value of the characteristic in the second liquid upstream of the exchanger; measuring, in each of the first and second treatment liquids, two values of the characteristic, respectively upstream and downstream of the exchanger; making a third treatment liquid flow through the exchanger while the characteristic of the second liquid has not reached a stable value downstream of the exchanger, the value of the characteristic in the third liquid upstream of the exchanger being different from the value of the characteristic in the second liquid upstream of the exchanger; measuring two values of the characteristic in the third liquid, respectively upstream and downstream of the exchanger; and computing at least one value of at least one parameter indicative of the progress of the treatment from the measured values of the characteristic in the first, second and third treatment liquids. Another method for the in vivo determination of the hemodialysis parameters which does not require taking measurements on blood samples is described in document EP 0920877. This method includes the steps of: making a treatment liquid flow through the exchanger, this treatment liquid having a characteristic which has an approximately constant nominal value upstream of the exchanger; varying the value of the characteristic upstream of the exchanger and then re-establishing the characteristic to its nominal value upstream of the exchanger; measuring and storing in memory a plurality of values adopted by the characteristic of the treatment liquid downstream of the exchanger in response to the variation in the value of this characteristic caused upstream of the exchanger; determining the area of a downstream perturbation region bounded by a baseline and a curve representative of the variation with respect to time of the characteristic; and computing the parameter indicative of the effectiveness of a treatment from the area of the downstream perturbation region and from the area of an upstream perturbation region bounded by a baseline and a curve representative of the variation with respect to time of the characteristic upstream of the exchanger.

The above described methods require a relatively short—compared to treatment time—modification of the value of a characteristic of the dialysis liquid (the conductivity, for example) and then the re-establishment of this characteristic to its initial value, which is generally the prescribed value. Since, deviations from the prescription are not desirable and since the above described methods require a minimum duration of the introduced modification, it derives that all these methods can be carried out only few times during a treatment.

With the aim of further improving the above methods, document US 2001004523 describes a solution for continuously determining a parameter (D, Cbin, K, KT/V) indicative of the effectiveness of an extracorporeal blood treatment comprising the steps of: causing a succession of sinusoidal variations in the characteristic (Cd) a treatment liquid upstream of the exchanger, continuously storing in memory a plurality of values ($Cd_{in1}$ ... $Cd_{in}$ ... $Cd_{inp}$) of the characteristic (Cd) upstream of the exchanger, measuring and continuously storing in memory a plurality of values ($Cd_{out1}$, ... $Cd_{outj}$ ... $Cd_{outp}$) adopted by the characteristic (Cd) downstream of the exchanger in response to the variations in the characteristic (Cd) which are caused upstream of the exchanger, computing—each time that a predetermined number of new values ($Cd_{outj}$) of the characteristic (Cd) downstream of the exchanger has been stored—a parameter (D, Cbin, K, KT/V) indicative of the effectiveness of the extracorporeal blood treatment, from a first series of values ($Cd_{inj}$) of the characteristic (Cd) upstream of the exchanger, from a second series of values ($Cd_{outj}$) of the characteristic (Cd) downstream of the exchanger, based on a mathematical model of the influence of the characteristic (Cd) on the effectiveness of the treatment.

Finally, EP2687248 describes an apparatus configured to calculate values of a parameter relating to treatment effectiveness based on measures of the conductivity in the spent dialysate line subsequent to an alternating conductivity perturbation continuously imposed on the preparation line of fresh dialysis fluid.

The advantage of a alternated perturbations in the characteristic of the liquid upstream the dialyzer is that the patient may not be exposed to a treatment liquid very different from the prescribed treatment liquid (for example, one which is too rich or too depleted in sodium).

Although the above methods resulted in certain improvements over the state of the art, the known solutions still need to perturb the composition of the dialysis liquid.

Furthermore, the characteristic in the liquid downstream the dialyzer may be difficult to accurately be measured. Moreover, the hydraulic delay, the damping effect caused by the dialyzer, and the noise introduced by the machine and its components may require to appropriately elaborate the signals detected by the sensors.

It is therefore an object of the present invention to provide an apparatus and a method to reliably calculate an effectiveness parameter during treatment without impairing on the treatment prescription.

Moreover, it is an auxiliary object providing a method and an apparatus which are not very sensitive to incidents or noise or accidental detection errors.

Additionally, it is an object providing a method and an apparatus which may be implemented with no need of high computational power and without complex mathematical models.

Another auxiliary object is an apparatus capable of operating in a safe manner.

A further auxiliary object is an apparatus capable of automatically calculate the parameter and inform the operator accordingly.

SUMMARY

At least one of the above objects is substantially reached by an apparatus according to one or more of the appended claims.

Apparatus and processes according to aspects of the invention and capable of achieving one or more of the above objects are here below described.

A $1^{st}$ aspect concerns an apparatus for extracorporeal treatment of blood comprising: a preparation line (19) having one end configured for being connected to an inlet of a secondary chamber (4) of a treatment unit (2), a semipermeable membrane (5) separating said secondary chamber (4) from a primary chamber of the same treatment unit (2); a spent dialysate line (13) having one end configured for being connected to an outlet of said secondary chamber (4); a control unit (10) configured for commanding execution of the following steps:

causing a fresh treatment liquid to flow in the preparation line (19) towards the secondary chamber (4) at a flow rate ($Qd_{in}$), the treatment liquid including lactate or citrate or acetate;

causing a used treatment liquid to flow in the spent dialysate line (13) at a flow rate ($Qd_{out}$);

receiving one or more measured values of a parameter related to the concentration of lactate or citrate or acetate ($Cd_{out}$) in the used treatment liquid flowing in the spent dialysate line (13);

computing at least one value of a parameter (D, KT) indicative of the effectiveness of the extracorporeal blood treatment based on:

said one or more measured values of the parameter related to the concentration of lactate or citrate or acetate ($Cd_{out}$) of the used treatment liquid;

at least one of: said flow rate ($Qd_{in}$) of fresh treatment liquid and said flow rate ($Qd_{out}$) of used treatment liquid.

In a $2^{nd}$ aspect according to the $1^{st}$ aspect, the control unit is further configured for receiving one or more values of a parameter related to the concentration of lactate or citrate or acetate ($Cd_{in}$) of the fresh treatment liquid flowing in the preparation line (19). This step of receiving may include measuring one or more actual values, or retrieving from a memory one or more preset values, or receiving from a user interface one or more input values of the parameter related to the concentration of lactate or citrate or acetate ($Cd_{in}$) of the fresh treatment liquid flowing in the preparation line (19).

In a $3^{rd}$ aspect according to the $2^{nd}$ aspect computing at least one value of a parameter (D, KT) indicative of the effectiveness of the extracorporeal blood treatment is based on:

said one or more measured values of the parameter related to the concentration of lactate or citrate or acetate ($Cd_{out}$) of the used treatment liquid;

said one or more values of the parameter related to the concentration of lactate or citrate or acetate ($Cd_{in}$) of the fresh treatment liquid;

at least one of: said flow rate ($Qd_{in}$) of fresh treatment liquid and said flow rate ($Qd_{out}$) of used treatment liquid.

In a $4^{th}$ aspect according to any one of the preceding aspects, the step of causing a fresh treatment liquid to flow in the preparation line (19) comprises the sub-step of maintaining, at least for a time interval ($\Delta T$), the concentration of the lactate or citrate or acetate ($Cd_{in}$) in the fresh treatment liquid constant at a set value ($Cd_{set}$) which represents the value of the parameter related to the concentration of lactate or citrate or acetate ($Cd_{in}$) of the fresh treatment liquid used for computing the at least one value of a parameter (D, KT) indicative of the effectiveness of the extracorporeal blood treatment.

In a 5th aspect according to the preceding aspect said one or more measured values of the parameter related to the concentration of lactate or citrate or acetate ($Cd_{out}$) in the used treatment liquid are representative of measures of the parameter related to the concentration of lactate or citrate or acetate ($Cd_{out}$) taken either during said time interval ($\Delta T$).

In a $6^{th}$ aspect according to the $4^{th}$ aspect said one or more measured values of the parameter related to the concentration of lactate or citrate or acetate ($Cd_{cut}$) in the used treatment liquid are representative of measures of the parameter related to the concentration of lactate or citrate or acetate ($Cd_{out}$) taken during a further time interval ($\Delta T'$), optionally having same duration of said time interval, delayed by an hydraulic delay with respect to said time interval. The hydraulic delay is the time required by a unitary mass of fluid to move from a predetermined section in the fluid preparation line to the section in the fluid spent line where measures are taken.

In a $7^{th}$ aspect according to any one of the preceding aspects, the control unit (10) is further configured for:
receiving a total treatment time (Tt), which is a time during which the apparatus operates with blood in the extracorporeal circuit and a patient connected to the extracorporeal circuit,
maintaining the concentration of the lactate or citrate or acetate in the fresh treatment liquid constant at said set value ($Cd_{set}$) during a time interval ($\Delta T$) lasting for a significant portion of the treatment time (Tt) and
calculating a plurality of consecutive times during said time interval ($\Delta T$) the value of the parameter (D, KT) indicative of the effectiveness of the extracorporeal blood treatment.

In a $8^{th}$ aspect according to the preceding aspect, said significant portion of the treatment time comprises one in the group of:
at least 10% of said total treatment time (Tt),
at least 30% of said total treatment time (Tt),
at least 70% of said total treatment time (Tt),
the entire treatment total time (Tt).

In a $9^{th}$ aspect according to any one of the preceding aspects, the apparatus comprises an outlet lactate or citrate or acetate concentration sensor (50) connected to the control unit (10); wherein the outlet lactate or citrate or acetate concentration sensor (50) is configured for measuring one or more real values of the concentration taken by lactate or citrate or acetate in the fluid exiting from the secondary chamber (4) and wherein the control unit (10) is configured to receive, as measured value or values of the parameter related to the concentration of lactate or citrate or acetate ($Cd_{out}$) in the used treatment liquid, the one or more measured real values of the lactate or citrate or acetate concentration detected by the lactate or citrate or acetate concentration sensor (50).

In a $10^{th}$ aspect according to the preceding aspect, the outlet lactate or citrate or acetate concentration sensor is operative at said spent dialysate line (13) or on a line connected to the spent dialysate line (13) or to the outlet of said secondary chamber (4).

In an $11^{th}$ aspect according to any one of the preceding aspects, the apparatus includes at least a blood pump configured to operate on an extracorporeal blood circuit connectable to the primary chamber of said blood treatment unit, said control unit being connected to the blood pump and being configured to:
operate the blood pump to cause flow of a patient's blood in the extracorporeal blood circuit at a blood flow rate (Qb),
receive or store a value representative of the concentration of lactate in blood or in a blood component ($Cb_{in}$).

In a $12^{th}$ aspect according to any one of the preceding aspects, the parameter (D, KT) indicative of the effectiveness of the extracorporeal blood treatment is calculated based on:
at least one measured value of the parameter related to the concentration of lactate or citrate or acetate ($Cd_{out}$) in the used treatment liquid;
at least one measured value of the parameter related to the concentration of lactate or citrate or acetate ($Cd_{in}$) of the fresh treatment liquid;
said flow rate ($Qd_{in}$) of fresh treatment liquid;
said value representative of the concentration of lactate or or citrate or acetate in blood or in a blood component ($Cb_{in}$).

In a $13^{th}$ aspect according to any one of the preceding aspects from the $5^{th}$ to the $12^{th}$, the control unit—at least during said time interval ($\Delta T$) or during said further time interval ($\Delta T'$)—is configured to keep constant the flow rate ($Qd_{in}$) of fresh treatment liquid in the preparation line (19), the flow rate (Qb) of patient's blood in the extracorporeal blood circuit, the flow rate ($Q_F$) of ultrafiltration flow through the semipermeable membrane (for instance the ultrafiltration flow rate may be kept at zero).

In a $14^{th}$ aspect according to any one of the preceding aspects the parameter indicative of the effectiveness of the extracorporeal blood treatment is lactate or citrate or acetate dialysance (D).

In a $15^{th}$ aspect according to the preceding aspect lactate or citrate or acetate dialysance (D) is calculated using the following formula:

$$D=(Qd\text{in}\times(Cd\text{in } Cd\text{out})+QF\times Cd\text{out})/(Cd\text{in } Cb\text{in})$$

where
D is the calculated value of dialysance for lactate or citrate or acetate,
$Cd_{out}$ is the measured value of the parameter related to the concentration of lactate or citrate or acetate, in particular the lactate or citrate or acetate concentration, of the used treatment liquid;
$Cd_{in}$ is measured value of the parameter related to the concentration of lactate or citrate or acetate, in particular the lactate or citrate or acetate concentration, of the fresh treatment liquid;
$Qd_{in}$ is the flow rate of fresh treatment liquid;
$Cb_{in}$ is the value representative of the concentration of lactate or citrate or acetate in blood or in a blood component;
$Q_F$ is the value of ultrafiltration flow rate through the semipermeable membrane.

In a $16^{th}$ aspect according to the preceding aspect, lactate or citrate or acetate dialysance—when no ultrafiltration through the semipermeable membrane is present ($Q_F$=0)—is calculated as follows:

$$D=D0=(Qd\text{in}\times(Cd\text{in } Cd\text{out}))/(Cd\text{in } Cb\text{in})$$

In a $17^{th}$ aspect according to any one of the preceding aspects, the control unit is configured for causing the fresh treatment liquid to flow in the preparation line (19) towards the secondary chamber (4) at a constant lactate concentration ($Cd_{in}$), which is set at a set value ($Cd_{set}$) comprised between 35 mmol/l and 45 mmol/l.

In a 18th aspect according to any one of the preceding aspects, the control unit is configured for causing the fresh treatment liquid to flow in the preparation line (19) towards the secondary chamber (4) at a constant lactate concentration ($Cd_{in}$), which is set at a set value ($Cd_{set}$) comprised between 38 mmol/l and 42 mmol/l.

In a 19th aspect according to any one of the preceding aspects, the value ($Cb_{in}$) representative of the concentration of lactate in blood or in a blood component is a known value selected in the range comprised between 1 and 5 mmol/l.

In a 20th aspect according to any one of the preceding aspects, the one or more measured values of the parameter related to the concentration of lactate or citrate or acetate ($Cd_{out}$) of the used treatment liquid are taken after 30 minutes from start of the extracorporeal blood treatment.

In a 21th aspect according to any one of the preceding aspects, the parameter indicative of the effectiveness of the extracorporeal blood treatment is lactate dialysance (D), and the control unit is configured to calculate the dialysance for a given solute different from lactate from:
the calculated value of the lactate dialysance,
one or more established relationships between the value of mass transfer coefficient $(K0.A)_{lactate}$ for lactate to the value of mass transfer coefficient $(K0.A)_{solute}$ for the given solute, the mass transfer coefficient reflecting a solute diffusion through the membrane.

In a 22nd aspect according to any one of the preceding aspects, the parameter indicative of the effectiveness of the extracorporeal blood treatment is lactate dialysance (D), and the control unit is configured to calculate dialysance for a given solute different from lactate as follows:
deriving (302) a mass transfer coefficient for lactate $(K0.A)_{lactate}$ of the membrane of the treatment unit from the calculated value of the dialysance for lactate;
determining (303) a mass transfer coefficient $(K0.A)_{solute}$ of the membrane of the treatment unit for the given solute based on the value of the mass transfer coefficient $(K0.A)_{lactate}$ for lactate;
calculating (304) the dialysance for the given solute based on the mass transfer coefficient $(K0.A)_{solute}$ for the given solute.

In a 23rd aspect according to any one of the preceding two aspects, the lactate dialysance and the dialysance for a given solute different from lactate are calculated at same values of:
the flow rate ($Qd_{in}$) of fresh treatment liquid,
the ultrafiltration flow rate ($Q_F$) through the semipermeable membrane;
and making reference to a same blood flow rate (Qb) in the extracorporeal circuit.

In a 24th aspect according to any one of the preceding three aspects, the control unit is configured for:
identifying the solute for which dialysance is to be calculated,
determining if a mass transfer time of the solute through red blood cells is greater, optionally at least 5 times greater, than a blood dwell time of blood flowing through the blood treatment unit,
using the value of the plasma flow rate at the inlet of the blood treatment unit ($Qp_{in}$) as effective value of the blood flow rate for the purpose of calculating the solute mass transfer coefficient $(K0.A)_{lactate}$, if it has been determined that the mass transfer time of the solute through red blood cells is grater, optionally 5 times greater, than blood dwell time in blood treatment unit, where $Qp_{in}=(1-Hct) Qb_{in}$, with Hct being the hematocrit of blood in the arterial line at the inlet of the blood treatment unit and ($Qb_{in}$) the blood flow rate at the inlet of the blood treatment unit.

In a 25th aspect according to any one of the preceding four aspects, the mass transfer coefficient for lactate $(K0.A)_{lactate}$ of the membrane of the treatment unit is derived by:
measuring or calculating (301) the value of dialysance for lactate, in particular at zero ultrafiltration,
deriving (302) a mass transfer coefficient for lactate $(K0.A)_{lactate}$ of the membrane of the treatment unit from:
the calculated value of the dialysance for lactate, in particular at zero ultrafiltration,
one or more of values of: the flow rate ($Qd_{in}$) of fresh treatment liquid, the flow rate ($Qd_{out}$) of spent dialysate liquid, the ultrafiltration flow rate ($Q_F$) through the semipermeable membrane,
the blood flow rate (Qb) or the plasma flow rate (Qp), in particular one of the plasma flow rate at the inlet of the blood treatment unit ($Qp_{in}$) and the blood flow rate at the inlet of the blood treatment unit ($Qb_{in}$).

In a 26th aspect according to any one of the preceding five aspects, the mass transfer coefficient for lactate $(K0.A)_{lactate}$ of the membrane of the treatment unit is derived by:
measuring or calculating (301) the value of dialysance for lactate, at zero ultrafiltration,
deriving (302) a mass transfer coefficient for lactate $(K0.A)_{lactate}$ of the membrane of the treatment unit from:
the calculated value of the dialysance for lactate, at zero ultrafiltration,
one or more of values of: the flow rate ($Qd_{in}$) of fresh treatment liquid, the flow rate ($Qd_{out}$) of spent dialysate liquid, the ultrafiltration flow rate ($Q_F$) through the semipermeable membrane,
the blood flow rate (Qb) or the plasma flow rate (Qp), in particular one of the plasma flow rate at the inlet of the blood treatment unit
($Qp_{in}$) and the blood flow rate at the inlet of the blood treatment unit ($Qb_{in}$).

In a 27th aspect according to any one of the preceding six aspects, the mass transfer coefficient $(K0.A)_{solute}$ for the given solute is derived (303) using one or more established relationships, optionally one or more known ratios, between the value of the mass transfer coefficient $(K0.A)_{lactate}$ for lactate to the value of the mass transfer coefficient $(K0.A)_{solute}$ for the given solute.

In a 28th aspect according to any one of the preceding aspect, calculating dialysance of the given solute (304) comprises calculating said dialysance for the given solute based on:
one or more of values of: the flow rate ($Qd_{in}$) of fresh treatment liquid, the flow rate ($Qd_{out}$) of spent dialysate liquid, the ultrafiltration flow rate ($Q_F$) through the semipermeable membrane,
the blood flow rate (Qb) or the plasma flow rate (Qp), in particular one of the plasma flow rate at the inlet of the blood treatment unit ($Qp_{in}$) and the blood flow rate at the inlet of the blood treatment unit ($Qb_{in}$),
the determined mass transfer coefficient for the given solute $(K0.A)_{solute}$.

In a 29th aspect according to any one of the preceding four aspects, the step of deriving a mass transfer coefficient for lactate $(K0.A)_{lactate}$ of the membrane of the treatment unit comprises:
measuring or calculating (301) the value of dialysance for lactate at zero ultrafiltration, and
calculating (302) the mass transfer coefficient for lactate $(K0.A)_{lactate}$ of the membrane of the treatment unit using the calculated value of the dialysance for lactate at zero ultrafiltration.

In a 30th aspect according to any one of the preceding two aspects, the step of calculating dialysance of the given solute (304) comprises:

first determining the value of the dialysance for the given solute, at zero ultrafiltration, based upon:

the determined mass transfer coefficient for the given solute $(K0.A)_{solute}$;

one of: the flow rate $(Qd_{in})$ of fresh treatment liquid, the flow rate $(Qd_{out})$ of spent dialysate liquid;

the blood flow rate (Qb) or the plasma flow rate (Qp), in particular one of the plasma flow rate at the inlet of the blood treatment unit $(Qp_{in})$ and the blood flow rate at the inlet of the blood treatment unit $(Qb_{in})$;

then determining dialysance for the given solute at non zero ultrafiltration based on:

the determined value of the dialysance for the given solute at zero ultrafiltration, and the value of the ultrafiltration flow rate; or the determined value of the dialysance for the given solute at zero ultrafiltration, the value of the ultrafiltration flow rate $(Q_F)$ through the semipermeable membrane, and the blood flow rate (Qb) or plasma flow rate (Qp), in particular one of the plasma flow rate at the inlet of the blood treatment unit $(Qp_{in})$ and the blood flow rate at the inlet of the blood treatment unit $(Qb_{in})$.

In a 31st aspect according to any one of the preceding aspects, the parameter indicative of the effectiveness of the extracorporeal blood treatment based comprises lactate dialysis dose $(KT)_{lactate}$ delivered over a reference time period (T).

In a 32nd aspect according to the preceding aspect, the control unit (10) is configured to calculate lactate dialysis dose $(KT)_{lactate}$ by:

determining the total effluent volume flown in the spent dialysate line (EV) in the course of the reference time period (T), measuring the lactate concentration of said total effluent volume, calculating (KT) based on the lactate concentration in blood, lactate concentration in the fresh treatment liquid and lactate concentration in said effluent volume, optionally using the following formula:

$(KT)_{lactate}=EV*((Cd_{in}-Cd_{out})/(Cd_{in}-Cb_{in}))$ where
EV: effluent volume,
$Cd_{out}$ is the lactate concentration of the used treatment liquid;
$Cd_{in}$ is the lactate concentration of the fresh treatment liquid;
$Cb_{in}$ is the concentration of lactate in blood or in a blood component (plasma);

In a 33rd aspect according to the 31st aspect, the control unit (10) is configured to calculate lactate dialysis dose $(KT)_{lactate}$ by: receiving said one or more values of a parameter related to the concentration of lactate $(Cd_{in})$ of the fresh treatment liquid flowing in the preparation line (19) measured during the reference time period (T), receiving values of the following flow rates, which remain constant during the time period (T): blood flow rate (Qb), fresh treatment liquid flow rate $(Qd_{in})$ or used treatment liquid flow rate $(Qd_{out})$, and, if present, ultrafiltration flow rate $(Q_F)$, calculating a value of lactate dialysance $(D_{lactate})$ for said time period (T), calculating a lactate dialysis dose $(KT)_{lactate}$ for said time period (T) multiplying the duration of the time period (T) times the lactate dialysance $(D_{lactate})$ determined for the same time period (T).

In a 34th aspect according to any one of the preceding aspects, total treatment time (Tt) comprises a plurality of consecutive reference time periods (Ti), each reference time period (Ti) being a fraction of the total treatment time, further wherein blood flow rate (Qb), fresh treatment liquid flow rate $(Qd_{in})$, used treatment liquid flow rate $(Qd_{out})$ and, if present, ultrafiltration flow rate $(Q_F)$ remain constant at respective values during each respective of said consecutive reference time periods (Ti).

In a 35th aspect according to the preceding aspect, the total dialysis dose for lactate $(KTt)_{lactate}$ is calculated as follows:

calculating for each of said time period a respective partial dialysis dose for lactate $(KT)i_{lactate}$, calculating the total dialysis dose for lactate $(KTt)_{lactate}$ making the sum of each partial dialysis dose for lactate $(KT)i_{lactate}$ for each reference time period Ti as follows: $(KTt)_{lactate}=\Sigma(K\,T)i_{lactate}$ In a 36th aspect according to the preceding aspect the total dialysis dose for lactate $(KTt)_{lactate}$ is calculated as follows:

calculating for each of said time period a respective partial dialysis dose for lactate $(KT)i_{lactate}$ using formula:

$(KT)i_{lactate}=EVi*((Cd_{in}-Cd_{out})/(Cd_{in}-Cb_{in}))$ where

EVi: effluent volume collected during each respective time interval (Ti), $Cd_{out}$ is the lactate concentration of the used treatment liquid during each respective time interval (Ti), $Cd_{in}$ is the lactate concentration of the fresh treatment liquid during each respective time interval (Ti), $Cb_{in}$ is the concentration of lactate in blood or in a blood component (plasma) during each respective time interval (Ti).

calculating the total dialysis dose for lactate $(KTt)_{lactate}$ making the sum of each partial dialysis dose for lactate $(KT)i_{lactate}$ for each reference time period Ti as follows:

$(KTt)_{Lactate}=\Sigma(K\,T)i_{lactate}$

In a 37th aspect according to the 35th aspect the control unit is configured to:

receiving said one or more values of a parameter related to the concentration of lactate $(Cd_{in})$ of the fresh treatment liquid flowing in the preparation line (19) measured during each reference time period (Ti), receiving values of the following flow rates, which remain constant during each time period (Ti): blood flow rate (Qb), fresh treatment liquid flow rate $(Qd_{in})$ or used treatment liquid flow rate $(Qd_{out})$, and, if present, ultrafiltration flow rate $(Q_F)$, calculating a value of lactate dialysance $(Di_{lactate})$ for each time period (Ti), calculating a lactate dialysis dose $(KT)i_{lactate}$ for each one of said time periods (Ti) multiplying the duration of each further time period (Ti) times the respective lactate dialysance $(Di_{lactate})$ determined for the same further time period (Ti);

summing the calculated lactate doses each of said time periods (Ti) to obtain the total lactate dose for the reference period: $\Sigma(K\ T)i_{lactate} = \Sigma(Di_{lactate} \cdot Ti)$ In a 38$^{th}$ aspect according to the preceding aspect, calculating (206) the value of the lactate dialysance ($Di_{lactate}$) for each time period (Ti) is made as follows:

calculating the value of dialysance ($Di_{lactate}$) at prescribed constant values of blood flow rate (Qb), fresh treatment liquid flow rate ($Qd_{in}$) or used treatment liquid flow rate ($Qd_{out}$) and, if present, ultrafiltration flow rate ($Q_F$);

calculating the mass transfer coefficient for lactate $(K0.A)_{Lactate}$;

based on the $(K0.A)_{lactate}$ and on respective constant values of blood flow rate (Qb), fresh treatment liquid flow rate ($Qdi_n$) or used treatment liquid flow rate ($Qd_{out}$) and, if present, ultrafiltration flow rate (QF) at each subsequent time period (Ti), calculating dialysance $(Di)_{lactate}$ for each subsequent of said time periods (Ti).

In a 39$^{th}$ aspect according to any one of the preceding aspects, the control unit (10) is configured to automatically trigger a new computation of the at least one value of said parameter (D, KT) indicative of the effectiveness of the extracorporeal blood treatment every time the control unit receives an indication that there has been a change or detects a change in one or more of following flow rates: blood flow rate (Qb), fresh treatment liquid flow rate ($Qdi_n$), used treatment liquid flow rate ($Qd_{out}$) and, if present, ultrafiltration flow rate ($Q_F$).

In a 40$^{th}$ aspect according to any one of the preceding aspects, the control unit (10) is configured to execute one or both of:

determine presence of recirculation at fistula level (step 204), calculate an amount of recirculation at fistula level (step 204), by comparing the computed value of the parameter (D, KT) indicative of the effectiveness of the extracorporeal blood treatment with a reference value for the same parameter.

In a 41$^{st}$ aspect according to the preceding aspect, wherein the reference value is a constant dialysance reference value or a reference value which is a lactate or citrate or acetate dialysance or a lactate or citrate or acetate dialysis dose for a same patient in a previous treatment.

In a 42$^{nd}$ aspect according to any one of the preceding aspects, the apparatus comprises said treatment unit (2), wherein:

the preparation line (19) has one end connected to an inlet of the secondary chamber (4) of the treatment unit (2), the spent dialysate line (13) has one end connected to the outlet of said secondary chamber (4), a blood withdrawal line (6) is connected at an inlet of the primary chamber (3) and a blood return line (7) is connected at an outlet of the primary chamber (3).

A 43$^{rd}$ aspect concerns a method of controlling an apparatus for extracorporeal treatment of blood, the apparatus being of the type disclosed in any one of the preceding claims.

A 44$^{th}$ aspect concerns a method of controlling an apparatus for extracorporeal treatment of blood, the apparatus being of the type comprising:

a preparation line (19) having one end configured for being connected to an inlet of a secondary chamber (4) of a treatment unit having a primary chamber (3) and said secondary chamber (4) separated by a semi-permeable membrane;

a spent dialysate line (13) having one end configured for being connected to an outlet of said secondary chamber (4);

a blood withdrawal line (6) connected at an inlet of the primary chamber (3); and a blood return line (7) connected at an outlet of the primary chamber (3).

In a 45$^{th}$ aspect according to any one of the preceding two aspects, the method comprises execution of the following steps:

causing a patient's blood to flow in the blood withdrawal line, in the primary chamber and in the blood return line, causing a fresh treatment liquid to flow in the preparation line (19) towards the secondary chamber (4) at a flow rate ($Qd_{in}$), the treatment liquid including lactate or citrate or acetate;

causing a used treatment liquid to flow in the spent dialysate line (13) at a flow rate ($Qd_{out}$);

receiving one or more measured values of a parameter related to the concentration of lactate or citrate or acetate ($Cd_{out}$) in the used treatment liquid flowing in the spent dialysate line (13);

computing at least one value of a parameter (D, KT) indicative of the effectiveness of the extracorporeal blood treatment based on:

said one or more measured values of the parameter related to the concentration of lactate or citrate or acetate ($Cd_{out}$) of the used treatment liquid;

at least one of: said flow rate ($Qd_{in}$) of fresh treatment liquid and said flow rate ($Qd_{out}$) of used treatment liquid.

In a 46$^{th}$ aspect according to the preceding aspect, the method comprises receiving one or more values of a parameter related to the concentration of lactate or citrate or acetate ($Cd_{in}$) of the fresh treatment liquid flowing in the preparation line (19);

computing at least one value of a parameter (D, KT) indicative of the effectiveness of the extracorporeal blood treatment based on:

said one or more measured values of the parameter related to the concentration of lactate or citrate or acetate ($Cd_{out}$) of the used treatment liquid;

said one or more values of the parameter related to the concentration of lactate or citrate or acetate ($Cd_{in}$) of the fresh treatment liquid;

at least one of: said flow rate ($Qd_{in}$) of fresh treatment liquid and said flow rate ($Qd_{out}$) of used treatment liquid.

In a 47$^{th}$ aspect according to any one of the preceding four aspects, the method comprises executing the steps the control unit of aspects from the 1$^{st}$ to the 42$^{nd}$ is configured to execute.

A 48$^{th}$ aspect concerns a data carrier including instructions executable by a control unit of a blood treatment apparatus, in particular the blood treatment apparatus of any one of claims of aspects from the 1$^{st}$ to the 42$^{nd}$, wherein the instructions are configured such that, when executed by the control unit, they cause execution of the method according to any one of aspects from the 43$^{rd}$ to the 47$^{th}$.

In a 49$^{th}$ aspect according to the preceding aspect, the data carrier is a RAM, a ROM, an EPROM, an optical or a magnetic disc, an electromagnetic wave, a mass memory storage device such as an Hard Disk or a flash memory bank.

Finally according to a 50$^{th}$ aspect, it is a currently preferred option to use a dialysis liquid containing lactate and to measure spent and optionally fresh dialysate lactate concentration for the determination of the effectiveness parameter. Alternatively, other suitable substances that have similar properties as lactate are citrate and acetate. It is however to be noted that their concentrations in the fresh treatment liquid (e.g. in the fresh dialysis fluids) are much smaller than lactate, (0 to 5 mmol/l for acetate and 0 to 2 mmol/l for citrate): therefore the concentration gradients for acetate or citrate between the dialysis liquid and patient blood is much smaller than for lactate, with the result that the measure of concentration of acetate or of citrate in the spent dialysate line may be more difficult and less accurate.

DESCRIPTION OF THE DRAWINGS

Aspects of the invention are shown in the attached drawings, which are provided by way of non-limiting example, wherein.

DETAILED DESCRIPTION

Figure 3:
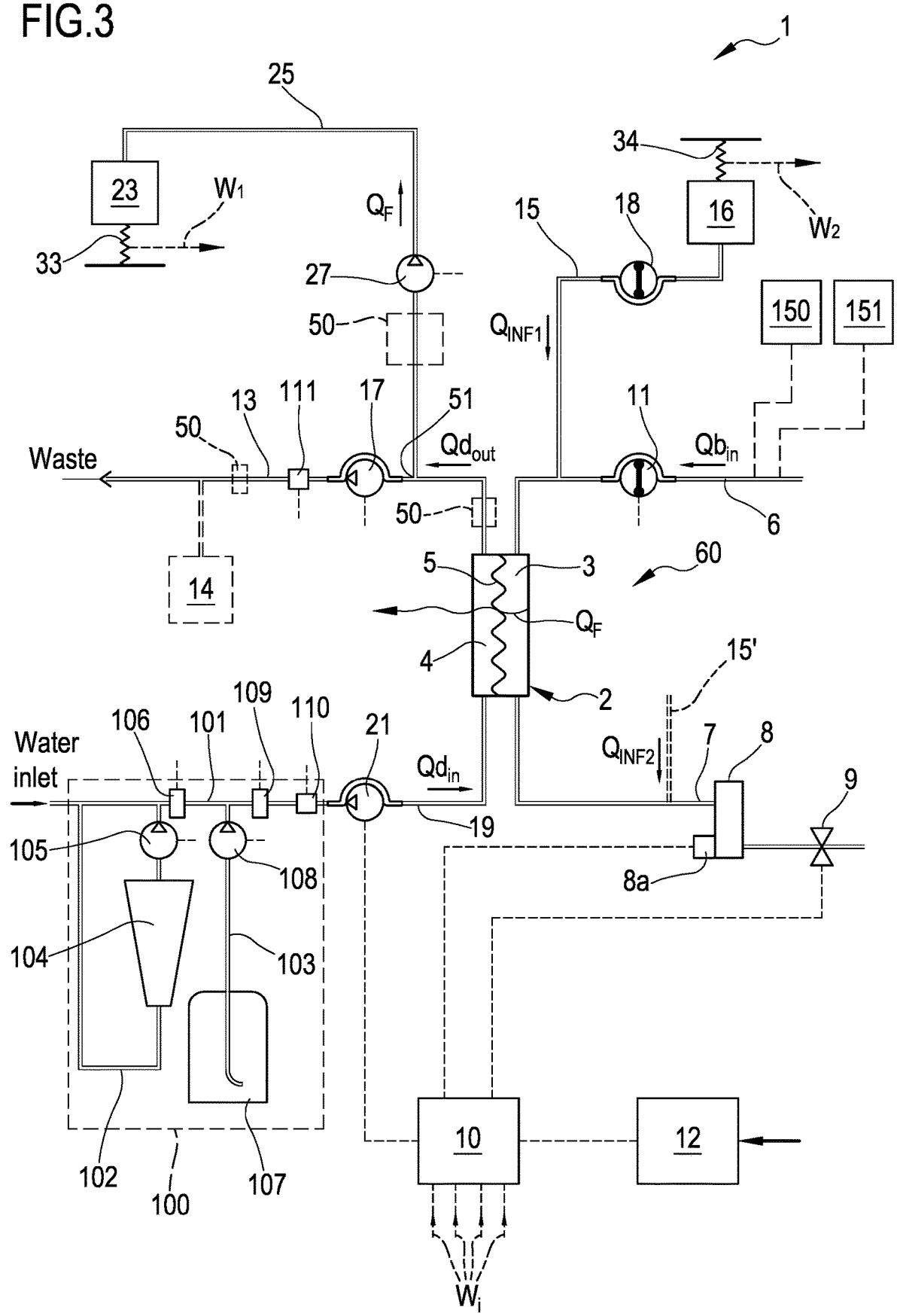
FIG. 3 shows a schematic diagram of a blood treatment apparatus according to one aspect of the invention.
Figure 4:
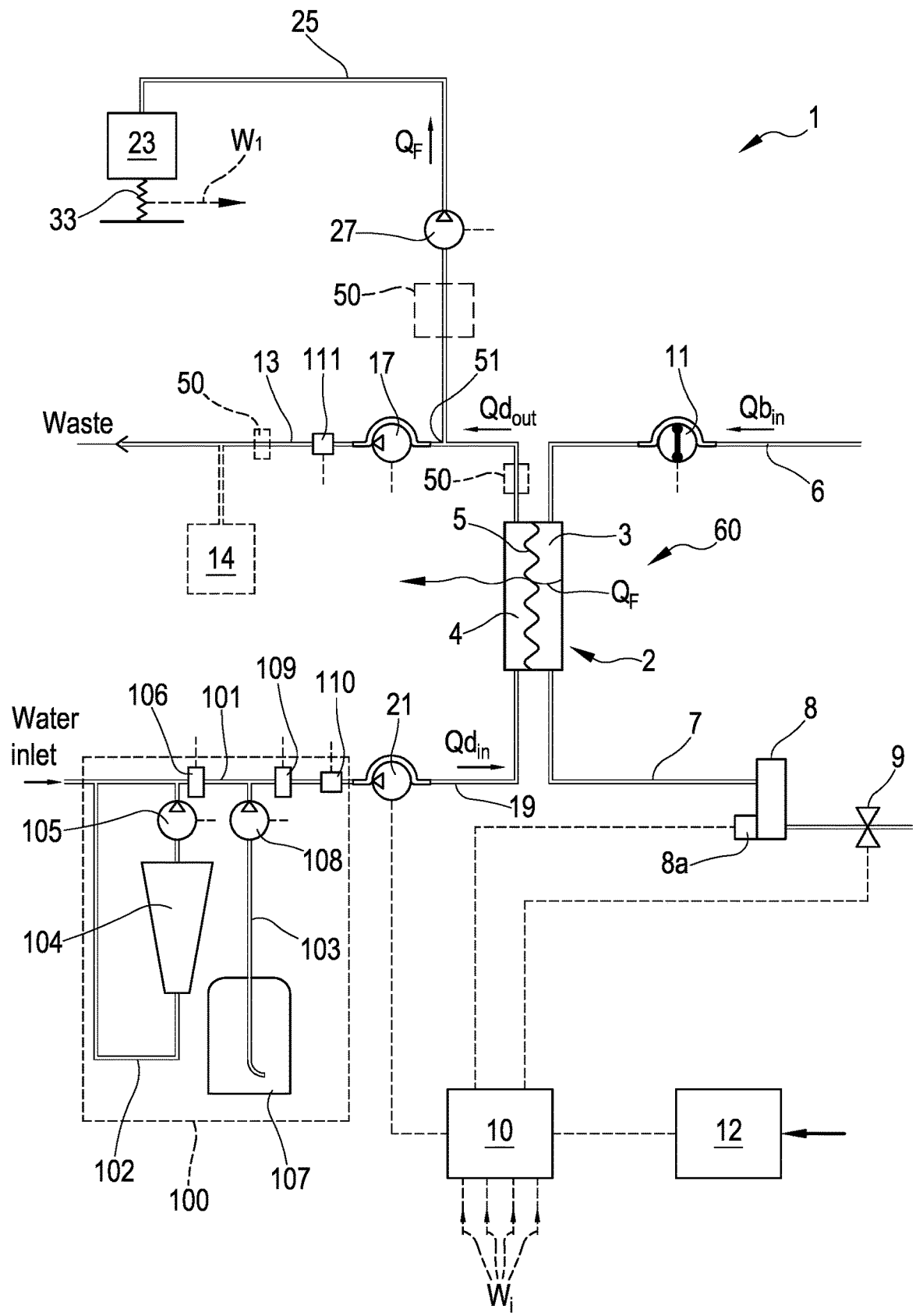
FIG. 4 shows a schematic diagram of an alternative embodiment of a blood treatment apparatus according to another aspect of the invention.

Non-limiting embodiments of an apparatus 1 for extracorporeal treatment of blood—which may implement innovative aspects of the invention—are shown in FIGS. 3 and 4. The apparatus 1 may be configured to determine a parameter indicative of the effectiveness of the treatment delivered to a patient (here below also referred to as 'effectiveness parameter'). In below description and in FIGS. 3 and 4 same components are identified by same reference numerals.

FIG. 3 shows an apparatus 1 configured to deliver any one of treatments like hemodialysis and hemodiafiltration, while FIG. 4 shows an apparatus configured to deliver hemodialysis or ultrafiltration treatments.

The apparatus 1 comprises a treatment unit 2 (such as a hemofilter, a hemodiafilter, a dialyzer and the like) having a primary chamber 3 and a secondary chamber 4 separated by a semi-permeable membrane 5; depending upon the treatment, the membrane of the filtration unit may be selected to have different properties and performances.

A blood withdrawal line 6 is connected to an inlet of the primary chamber 3, and a blood return line 7 is connected to an outlet of the primary chamber 3. In use, the blood withdrawal line 6 and the blood return line 7 are connected to a needle or to a catheter or other access device (not shown) which is then placed in fluid communication with the patient vascular system, such that blood may be withdrawn through the blood withdrawal line, flown through the primary chamber and then returned to the patient's vascular system through the blood return line. An air separator, such as a bubble trap 8 may be present on the blood return line; moreover, a safety clamp 9 controlled by a control unit 10 may be present on the blood return line downstream the bubble trap 8. The control unit may comprise a digital processor (CPU) and a memory (or memories), an analogical type circuit, or a combination thereof as explained in greater detail in below section dedicated to the 'control unit'. A bubble sensor 8a, for instance associated to the bubble trap 8 or coupled to a portion of the line 7 between bubble trap 8 and clamp 9 may be present: if present, the bubble sensor is connected to the control unit 10 and sends to the control unit signals for the control unit to cause closure of the clamp 9 in case one or more bubbles above certain safety thresholds are detected. As shown in FIG. 3, the blood flow through the blood lines is controlled by a blood pump 11, for instance a peristaltic blood pump, acting either on the blood withdrawal line (as shown in FIG. 3) or on the blood return line.

An operator may enter a set value for the blood flow rate Qb: the control unit 10, during treatment, is configured to control the blood pump based on the set blood flow rate. It is noted that the control unit 10 may also be connected to a user interface 12, for instance a graphic user interface, which receives operator's inputs (such as the set value for the blood flow rate) and displays the apparatus outputs. For instance, the graphic user interface 12 may include a touch screen for both displaying outputs and allowing user entries, or a display screen and hard keys for entering user's inputs, or a combination thereof.

A spent dialysate line 13 configured for evacuating an effluent fluid coming from the secondary chamber 4 is connected, at one end, to an outlet of the secondary chamber 4 and, at its other end, to a waste which may be a discharge conduit or an effluent fluid container 14 (dashed lines in FIGS. 3 and 4) collecting the fluid extracted from the secondary chamber. An effluent fluid pump 17 operates on the spent dialysate line under the control of control unit 10 to regulate the flow rate $Qd_{of}$ of effluent fluid exiting the secondary chamber 4 and flowing through the spent dialysate line. The apparatus may also include an ultrafiltration line 25 branching off the spent dialysate line 13 and provided with a respective ultrafiltration pump 27 also controlled by control unit 10 to cause a flow rate $Q_F$ along the ultrafiltration line. The embodiment of FIG. 3 presents a pre-dilution fluid line 15 connected to the blood withdrawal line: this line 15 supplies replacement fluid from an infusion fluid container 16 connected at one end of the pre-dilution fluid line. Although FIG. 3 shows a container 16 as source of infusion fluid, this should not be interpreted in a limitative manner: indeed, the infusion fluid may also come from an on line preparation section 100 part of the apparatus 1. Note that alternatively to the pre-dilution fluid line the apparatus of FIG. 3 may include a post-dilution fluid line (15' represented with dashed lines in FIG. 3) connecting an infusion fluid container or the on line preparation section to the blood return line. Finally, as a further alternative, the apparatus of FIG. 3 may include both a pre-dilution and a post infusion fluid line: in this case each infusion fluid line may be connected to a respective infusion fluid container or the two infusion fluid lines may receive infusion fluid from a same source of infusion fluid such as a same infusion fluid container or the online preparation section 100. In accordance with a possible variant, it is noted that the source of infusion fluid may be an online preparation section part of the apparatus 1 (i.e. the device 100 described herein below or a distinct device analogous to device 100 and connected to the infusion line or lines) supplying fluid to the post and/or pre dilution lines. Furthermore, an infusion pump 18 operates on the infusion line 15 to regulate the flow rate $Q_{INF1}$ through the infusion line 15. Note that in case of two infusion lines (pre-dilution and post-dilution) each infusion line may be provided with a respective infusion pump to regulate the respective flow rate $Q_{INF1}$, $Q_{INF2}$.

The apparatus of FIG. 3, further includes a fluid preparation line 19 connected at one end with a water inlet and at its other end with the inlet of the secondary chamber 4 of the filtration unit for supplying fresh treatment liquid to the secondary chamber 4. A dialysis fluid pump 21 works on the fluid preparation line under the control of said control unit 10, to supply fluid from a source of fresh treatment liquid (such as a container or the section 100 for on line preparing fresh dialysis liquid) to the secondary chamber 4 at a flow rate $Qd_{in}$.

In the example of FIGS. 3 and 4, the line 19 links the hemodialyzer or hemodiafilter 2 to a section 100 for preparing the dialysis liquid: section 100 comprises a main line 101, the upstream end of which is designed to be connected to a supply of water. A first secondary line 102 and a second secondary line 103 are connected to the main line 101 and are configured to at least supply the necessary quantity of a buffer and the necessary quantity of electrolytes. The first secondary line 102, which may be looped back onto the main line 101, is configured for fitting a first container 104, such as a bag or cartridge or other container, containing a buffer. Line 102 is furthermore equipped with a first metering pump 105 for dosing the buffer into the fresh treatment liquid: as shown in FIG. 3 the pump may be located downstream of the first container 104. The operation of the pump 105 may be controlled by the control unit 10 based upon the comparison between: 1) a set point value for the buffer concentration of the solution forming at the junction of the main line 101 and the first secondary line 102, and 2) the value of the buffer concentration of this mixture measured by a first probe 106 located either in the first secondary line downstream the first container 104 or in the main line 101 immediately downstream of the junction between the main line 101 and the first secondary line 102. Furthermore, the free end of the second secondary line 103 is intended to receive fluid from second container 107 containing a concentrated saline solution, e.g. electrolytes such as sodium chloride, calcium chloride, magnesium chloride and potassium chloride. In a variant also the second secondary line 103 may be looped back onto the main line. Moreover, it is possible envisaging a plurality of independent second secondary lines 103 in the case one wishes to feed separate electrolytes or electrolyte compositions from respective containers. Note that the second secondary line 103 is equipped with a second metering pump 108 for dosing electrolytes into the fresh treatment liquid; operation of the second metering pump depends on the comparison between 1) a conductivity setpoint value or an electrolyte concentration setpoint value for the solution forming at the junction of the main line 101 with the second secondary line 103, and 2) the value of the conductivity or electrolyte concentration of this solution measured by a second probe 109 located either in the second secondary line downstream of second container 107 or in the main line 12 immediately downstream of the junction between the main line 12 and the secondary line 103. Note that the specific nature of the concentrates contained in containers 104 and 107 may be varied depending upon the circumstances and of the type of fresh treatment fluid to be prepared. Moreover, the nature and the position of the first and second probes may depend upon the type of buffer used, the type of electrolyte concentrate(s) adopted and upon the specific configuration of the circuit formed by the main line and the secondary lines. Furthermore, as already mentioned, more than two secondary lines, with respective concentrate containers and respective metering pumps may be in case a plurality of different type of substances need to be added for the preparation of the fresh treatment fluid.

In accordance with one aspect of the present invention the buffer is or comprises lactate. In particular, the first container may host a lactate concentrate solution: the metering pump(s) and the dialysis pump may be controlled such as to generate a fresh treatment fluid at a desired lactate concentration (e.g. at 40 mmol/l of lactate concentration). Within the meaning of the present description and claims, lactate includes L-lactate, D-lactate, any mixture of D-lactate with L-lactate, or other lactate based compositions. Note that alternatively to the on line preparation section 100, the apparatus 1 may use one or more preformed bags of fresh treatment fluid at the desired concentration for the buffer (lactate) and for the substances (electrolytes, nutrients etcetera).

The embodiment of FIG. 4 shows an alternative apparatus 1 designed for delivering any one of treatments like hemodialysis and ultrafiltration. In the apparatus shown in FIG. 4 the same components described for the embodiment of FIG. 3 are identified by same reference numerals and thus not described again. In practice, differently from the hemodiafiltration apparatus of FIG. 3, the apparatus of FIG. 4 does not present any infusion line.

In each one of the above described embodiments, flow sensors 110, 111 (either of the volumetric or of the mass type) may be used to measure flow rate in each of the lines. Flow sensors are connected to the control unit 10. In the example of FIG. 3 where the infusion line 15 and the ultrafiltration line 25 lead to a respective container or bag 16, 23, scales may be used to detect the amount of fluid delivered or collected. For instance, the apparatus of figure includes a first scale 33 operative for providing weight information $W_1$ relative to the amount of the fluid collected in the ultrafiltration container 23 and a second scale 34 operative for providing weight information $W_2$ relative to the amount of the fluid supplied from infusion container 16. In the embodiment of FIG. 4, the apparatus includes a first scale 33 operative for providing weight information $W_1$ relative to the amount of the fluid collected in the ultrafiltration container 23. The scales are all connected to the control unit 10 and provide said weight information $W_i$ for the control unit to determine the actual quantity of fluid in each container as well as the actual flow rate of fluid supplied by or received in each container.

In the example of FIGS. 3 and 4, in order to control the fluid balance between the quantity of fluid supplied to the secondary chamber 4 and the quantity of fluid extracted from the secondary chamber, the flow-meters 110, 111 positioned on the fresh dialysate line 19 and on the spent dialysate line 13 provide the control unit with signals indicative of the flow of fluid through the respective lines and the scale or scales provide weight information which allow the control unit to derive the flow rate through the ultrafiltration line 25 and, if present, through the infusion line 15. The control unit is configured to control at least pumps 17, 21 and 27 (in case of FIG. 3 also pump 18) to make sure that a prefixed patient fluid removal is achieved in the course of a prescribed treatment time, as required by the prescription provided to the control unit, e.g. via user interface 12. Note that other fluid balance systems may be used: for instance in case the apparatus includes a container as source of fresh treatment fluid and a container to collect waste, then scales may be used to detect the amount of fluid delivered or collected by each container and then inform the control unit accordingly. As a further alternative, systems based on volumetric control may be used where the preparation line 19 and the spent dialysate line 13 are connected to a balance chamber system assuring that—at each instant—the quantity of liquid flowing into line 19 is identical to the quantity of fluid exiting from line 13.

From a structural point of view one or more, containers 104, 107, 16, 23 may be disposable plastic containers. The blood lines 6, 7 lines and the filtration unit may also be plastic disposable components which may be mounted at the beginning of the treatment session and then disposed of at the end of the treatment session. Pumps, e.g. peristaltic pumps or positive displacement pumps, have been described for regulating fluid flow through each of the lines; however, it should be noted that other flow regulating devices may alternatively be adopted such as for example valves or combinations of valves and pumps. The scales may comprise piezoelectric sensors, or strain gauges, or spring sensors, or any other type of transducer able to sense forces applied thereon. As already explained, the conductivity sensors may be replaced by concentration sensors.

Measure of the Parameter Indicative of Effectiveness of Blood Treatment

Figure 5:
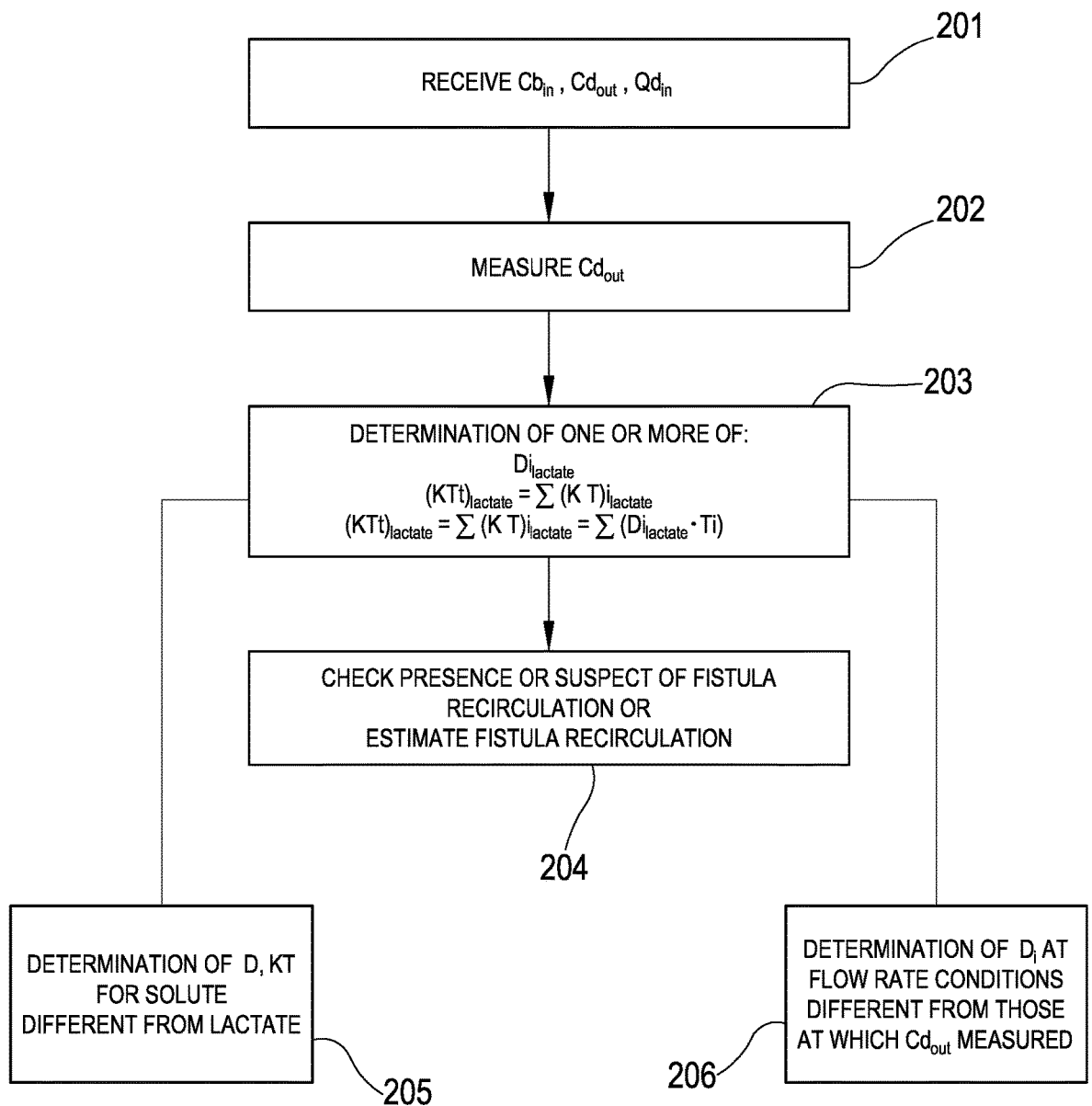
FIG. 5 is a schematic flowchart of a method according to one aspect of the invention.
Figure 6:
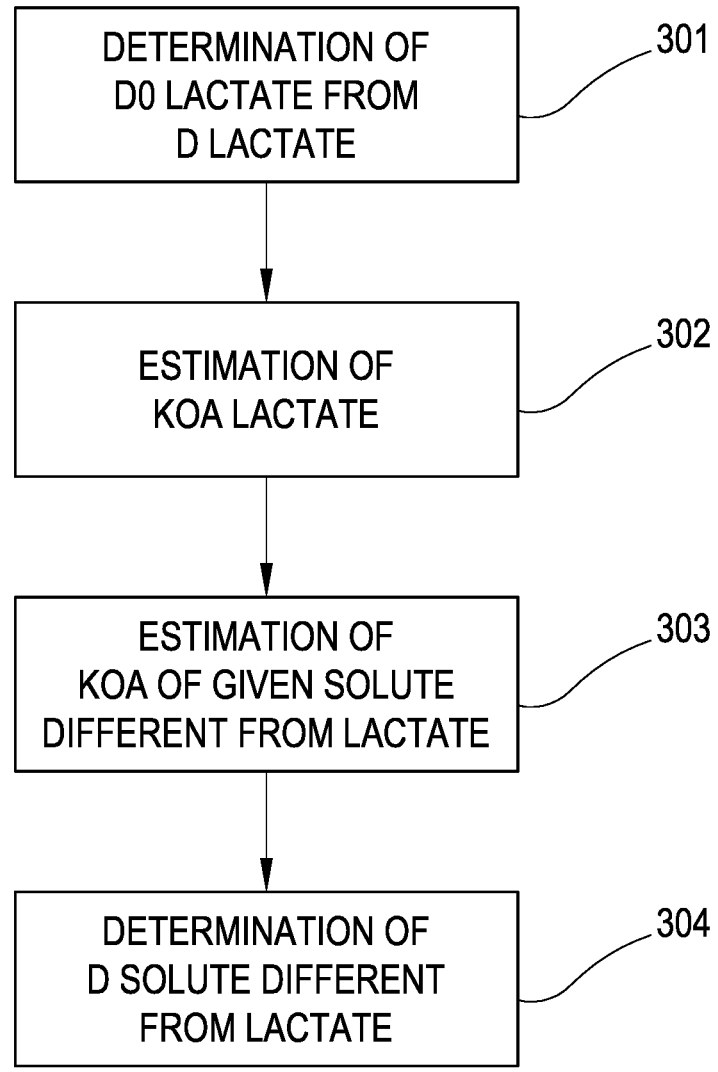
FIG. 6 is a schematic flowchart of a further method according to one aspect of the invention

The operation of the above apparatus for measuring a parameter indicative of the effectiveness of the blood treatment is now described, with reference to the attached figures and to the flowchart of FIGS. 5 and 6.

The control unit 10 is configured to operate the blood pump and cause flow of a patient's blood in the extracorporeal blood circuit at a blood flow rate Qb: for example the blood flow rate may be set by the user acting on the user interface 12, or it may be pre-stored in a memory associated to the control unit or it may be automatically calculated set by the control unit based on certain operative conditions (e.g. keeping pressure upstream the blood pump above a minimum threshold); the control unit 10 also commands pumps 105, 108 and 21 and is configured for causing the preparation of a treatment liquid in section 100 and the flow of the freshly prepared treatment liquid in line 19 and into the secondary chamber 4. The control unit may receive, e.g. via user interface 12, at least one prescription value $Cd_{set}$ for lactate concentration $Cd_{in}$ of the treatment liquid which should be kept during the treatment (step 201) and control the first metering pump accordingly. Note that the control unit 10 may also receive set values for the conductivity of the fresh treatment liquid, or for the concentration of at least one substance (e.g. sodium and/or other electrolytes) in the fresh treatment liquid and, based on this value(s), control the second and any further metering pump(s) accordingly.

Figure 1:
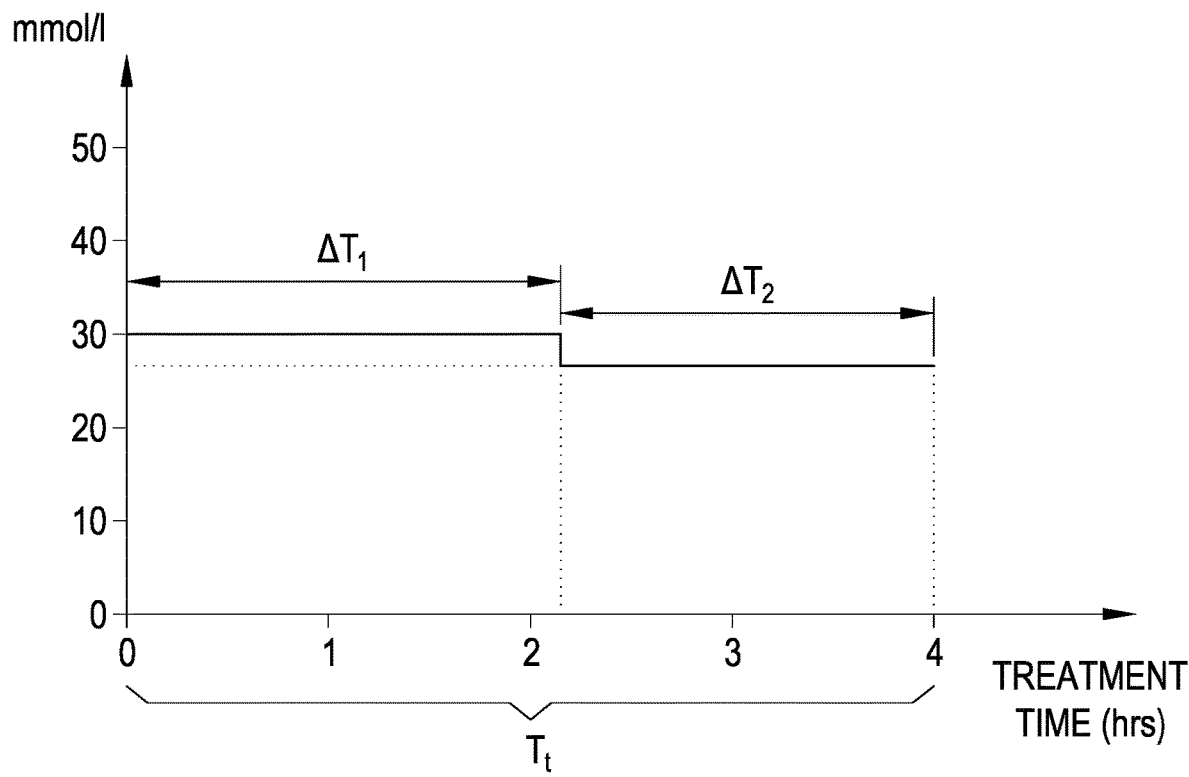
FIG. 1 shows a concentration vs. time diagram showing the profile of the concentration of lactate in the fresh dialysate line, according to an aspect of the invention.
Figure 2:
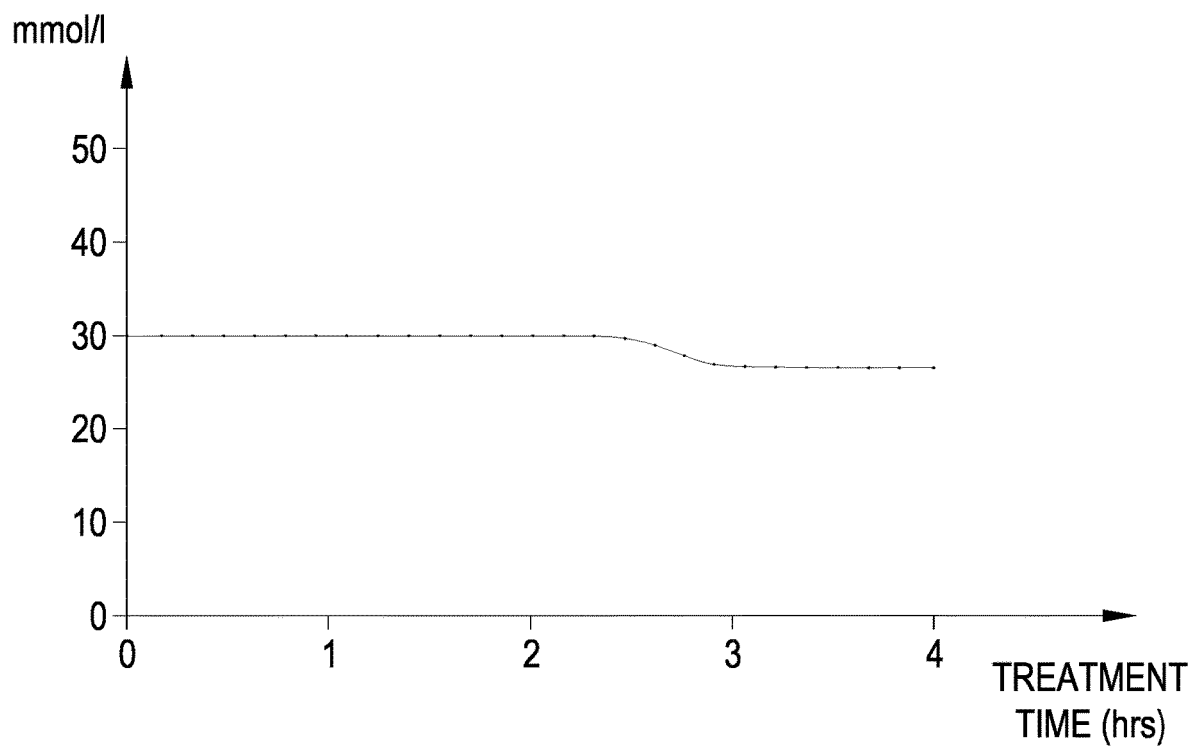
FIG. 2 shows a concentration vs. time diagram showing the profile of the concentration of lactate in the spent dialysate line, according to another aspect of the invention.

Note that the prescription value for lactate concentration or for other substances may be constant or it may vary according to a prefixed profile during the treatment. FIG. 1 shows the case of a prescription for lactate which is constant during a first portion of treatment at a set value of 40 mmol/l and then moved to a set value of 35 mmol/l for a second portion of the treatment. FIG. 2 shows the behavior of lactate concentration in the spent dialysate line 13 in a case where the prescription for lactate of FIG. 1 is imposed in the fresh treatment liquid in fluid preparation line 19 The control unit 10 is also configured for supplying fresh treatment fluid to the secondary chamber 4 at flow rate $Qd_{in}$ and for causing a used treatment liquid to exit the chamber 4 and flow in the spent dialysate line 13 at flow rate $Qd_{out}$: in other words the control unit is configured to receive or calculate the desired value for effluent flow rate $Qd_{out}$ and to command the effluent pump 17 accordingly, and to receive or calculate the desired value of flow rate of fresh treatment liquid $Qd_{in}$ and to command pump 21 accordingly. The control unit 10 is also responsible for controlling the ultrafiltration pump (if present) and any infusion line 18 (if present) in order to cause a flow of effluent fluid through the ultrafiltration line and a flow of infusion fluid through the one or more infusion lines. Note that for instance the control unit 10 may be configured to receive set values (e.g. via the user interface 12) for a number of fluid flow rates (e.g., one or more of $Q_{INF1}$, $Q_{INF2}$, $Q_F$, $Qd_{in}$, $Qd_{out}$, $Q_{WLR}$ this latter being representative of the weight loss rate), or corresponding volumes for each fluid, and calculate the set values for the remaining fluid flow rates based on desired conditions or prescriptions.

For example, referring to FIG. 3, considering that:

$$Q_F = Q_{INF1} + Q_{INF2} + Q_{WLR} \qquad \text{Equation (1)}$$

$$Qd_{in} = Qd_{out} - Q_F \qquad \text{Equation 1A}$$

the control unit may receive set values for n−2 of said flow rates ($Q_{INF1}$, $Q_{INF2}$, $Q_F$, $Qd_{in}$, $Qd_{out}$, $Q_{WLR}$), and calculate the remaining 2 using equations 1 and 1A.

The above also applies to the configuration of FIG. 4 noting that absent any infusion then:

$$Q_F = Q_{WLR} \qquad \text{Equation 1}$$

$$Qd_{in} = Qd_{out} - Q_F \qquad \text{Equation 1A}$$

and therefore it is sufficient for the control unit to know for example the value of the desired weight loss rate and that of one of $Qd_{in}$, $Qd_{out}$ to have all settings necessary to control the apparatus fluid lines.

In accordance with aspects of the invention, the control unit 10 is further configured for receiving one or more values of a parameter related to the concentration of lactate $Cd_{in}$ of the fresh treatment liquid flowing in the preparation line 19: for instance control unit 10, e.g. acting on preparation section 100, may keep the concentration of the lactate $Cd_{in}$ in the fresh treatment liquid constant at a set value $Cd_{set}$ (e.g., imposed by the operator via user interface 12). $Cd_{set}$ would therefore represent the value of the parameter related to the concentration of lactate $Cd_{in}$ of the fresh treatment liquid. In most treatments, the concentration of lactate in the fresh treatment liquid is kept at a same set value $Cd_{set}$ all along the treatment time Tt; it is however not excluded that the concentration of lactate in the fresh dialysis liquid may be changed and e.g., kept at a first constant value $Cd_{set1}$ for a time interval $\Delta T_1$ and then moved up or down to a different constant value $Cd_{set2}$ for a subsequent time interval $\Delta T_2$ (see FIG. 1). For example the control unit may keep the concentration of lactate in the fresh treatment liquid constant at said set value $Cd_{set}$ during a time interval $\Delta T$ lasting at least 10% of said total treatment time Tt, or at least 30% of said total treatment time Tt or at least 70% of said total treatment time Tt, or the entire treatment total time Tt. In most practical cases, the control unit may be configured for keeping the fresh treatment liquid at a concentration of lactate $Cd_{in}$ fixed at a set value $Cd_{set}$ comprised between 35 mmol/l and 45 mmol/l, preferably between 40 mmol/l and 45 mmol/l.

The control unit 10 is also configured for receiving one or more measured values of a parameter related to the concentration of lactate $Cd_{out}$ in the used treatment liquid flowing in the spent dialysate line 13 and for computing at least one value of a parameter D, KT indicative of the effectiveness of the extracorporeal blood treatment. At this purpose, the apparatus 1 may include an outlet lactate concentration sensor 50, which may be operative at said spent dialysate line 13 and be connected to the control unit: this latter is configured to receive, as measured value or values, of the parameter related to the concentration of lactate $Cd_{out}$ in the used treatment liquid, one or more measured values of the lactate concentration $Cd_{out}$ detected in real time by the lactate concentration sensor. Use of a lactate concentration sensor 50 located in the spent dialysate line 13 allows to measure the instantaneous value of lactate concentration and thus the control unit 10 may be configured to receive said measured value(s) of instantaneous lactate concentration(s) and to calculate in real time instantaneous value(s) of the parameter D, KT indicative of the effectiveness of the extracorporeal blood treatment. This may be repeated a plurality of times in the course of the treatment thereby monitoring in real time the value of the effectiveness parameter, still with no negative impact on treatment prescription as lactate concentration may follow its prescribed value. The lactate concentration sensor 50 may be located in the spent dialysate line itself: for instance the lactate concentration sensor 50 may be located in a tract of the spent dialysate line upstream the branch off point 51 of the ultrafiltration line 25 (see FIGS. 3 and 4) or it may be located on the spent dialysate line 13 downstream the branch off point 51 of the ultrafiltration line (see FIGS. 3 and 4 where sensor is represented in dashed tract on line 13). Alternatively, the sensor 50 may be located on a line branching off the spent dialysate line such as on ultrafiltration line 25 or on any other line branching off the spent dialysate line and configured to receive the fluid or part of the fluid flowing in the spent dialysate line.

In case of evaluation of a whole treatment session, then it may alternatively be envisaged to collect the spent fluid which has flown in the spent dialysate line (or samples of said spent fluid sampled at regular intervals) and measure the concentration of lactate in the collected fluid with an appropriate sensor. For example, in the circuit shown in FIGS. 3 and 4 the fluid collected in container 23 or in container 14 may be representative of the fluid that has flown in the spent dialysate line during the treatment.

In further detail and with reference to the flow chart of FIG. 5, in the case where the efficiency parameter is monitored in real time, the control unit may be configured for keeping the concentration of lactate in the fresh treatment liquid $Cd_{in}$ constant at said set value $Cd_{set}$ during a time interval $\Delta T$ (step 201) and for receiving one or more measured values of a parameter related to the concentration of lactate $Cd_{out}$ of the used treatment liquid flowing in the spent dialysate line from said sensor 50 (step 202); in particular, the measurements of the parameter related to the concentration of lactate $Cd_{out}$ are taken during the time interval $\Delta T$ or during a further time interval $\Delta T'$ having same duration of said time interval $\Delta T$ but delayed of an hydraulic delay with respect to said time interval. In other words, the measures of the value(s) $Cd_{out}$ in the used treatment liquid are related to a liquid which corresponds to the fresh treatment liquid at the known value $Cd_{set}$ of lactate concentration after this fresh liquid has passed through the secondary chamber of the blood treatment unit and reached the lactate concentration sensor.

As mentioned, (step 203) the control unit 10 may then calculate the effectiveness parameter D, KT: the calculation may be done a plurality of consecutive times during said time interval $\Delta T$ in order to get a reliable indication of the development of the actual effectiveness of the treatment. In particular, the control unit then calculates the value of the parameter D, KT indicative of the effectiveness of the extracorporeal blood treatment based on:

the one or more measured values of the parameter related to the concentration of lactate $Cd_{out}$ of the used treatment liquid;

the one or more values of the parameter related to the concentration of lactate $Cd_{in}$ of the fresh treatment liquid (in practice based on $Cd_{set}$);

the value of said flow rate $Qd_{in}$ of fresh treatment liquid or of said flow rate $Qd_{out}$ of used treatment liquid.

Additionally, the control unit may receive or store a value representative of the concentration of lactate in blood $Cb_{in}$: this value may be a constant value or a value set by the physician based on knowledge of the specific patient. The applicant noted that lactate concentration in arterial blood at the beginning of a treatment session is slightly less than 1 mmol/l and changes only slightly during the dialysis session: the average increase being between 2 and 4 mmol/liter and taking place in the first minutes of blood treatment. This means that if the calculation is made using measured values taken after the initial minutes of extracorporeal blood treatment, then considering as set value for the lactate concentration in blood e.g. 4 mmol/l does not significantly affect accuracy of the calculation of the effectiveness parameter. Thus, the control unit may accurately calculate the value of the parameter D, KT indicative of the effectiveness of the extracorporeal blood treatment based on the above indicated values and also on the value of the concentration of lactate in blood $Cb_{in}$, which is normally taken between 3 and 5 mmol/l.

In accordance with an aspect the parameter indicative of the effectiveness of the extracorporeal blood treatment is lactate dialysance D, and in particular effective lactate dialysance, which is calculated using the following formula:

$$D = (Qd\text{in} \times (Cd\text{in} - Cd\text{out}) + QF \times Cd\text{out})/(Cd\text{in} - Cb\text{in}) \quad \text{Equation (2)}$$

where

D is the calculated value of dialysance for lactate, $Cd_{out}$ is the measured value of the parameter related to the concentration of lactate, in particular the lactate concentration, of the used treatment liquid;

$Cd_{in}$ is measured value of the parameter related to the concentration of lactate, in particular the lactate concentration, of the fresh treatment liquid;

$Qd_{in}$ is the flow rate of fresh treatment liquid;

$Cb_{in}$ is the value representative of the concentration of lactate in blood or in a blood component (plasma);

$Q_F$ is the value of ultrafiltration flow rate through the semipermeable membrane.

When no ultrafiltration through the semipermeable membrane is present ($Q_F = 0$), then the above formula takes the following simplified form:

$$D = D0 = (Qd\text{in} \times (Cd\text{in} - Cd\text{out}))/(Cd\text{in} - Cb\text{in}) \quad \text{Equation (3)}$$

Note that for the purpose of calculation of the effectiveness parameter and in particular of dialysance the control unit is configured to keep constant both the flow rate $Qd_{in}$ of fresh treatment liquid in the preparation line 19 and the flow rate Qb of patient's blood in the extracorporeal blood circuit; in practice while the measure(s) of $Cd_{out}$ is/are taken (e.g., during $\Delta T$ or $\Delta T'$), the concentration $Cd_{in}$ of lactate in the fresh treatment liquid and the flow rates of fresh treatment liquid $Qd_{in}$ and of blood Qb are all kept constant.

The above calculated value of D is an effective dialysance and thus accounts for both the performances of the membrane of the blood treatment unit and for any recirculation at access level (i.e. recirculation of treated blood between the venous or return line and the arterial or withdrawal line of the extracorporeal blood circuit).

The control unit may also be configured to determine presence or at least a suspect of the presence of recirculation at fistula level and/or to calculate an amount of recirculation at fistula level (step 204) by comparing the detected dialysance value D with a reference value (which may be a constant reference value or a value of dialysance measured for the same patient in previous treatments).

Once the dialysance for lactate has been calculated, the control unit may also calculate and display (e.g., via user interface 12) the dialysance for a given solute different from lactate (step 205).

In greater detail, according to a further aspect of the invention and with reference to FIG. 6, the control unit 10 is configured to calculate dialysance for a given substance different from lactate (e.g., urea dialysance) based on the calculated value of the dialysance for lactate. The purpose of calculating $D_{solute}$ (or $K_{solute}$) for a solute different from lactate may be that of allowing to estimate the solute dialysis dose $(KT)_{solute}$, for example for a solute like urea. Note that while clearance and dialysance are dimensionally expressed as flow rates (e.g., mL/min), dialysis dose is usually expressed as KT/V (which is a "dimensionless ratio") or in a non-normalized manner simply as KT (which is a volume and can be expresses e.g., in mL or Liters), where:

K—dialyzer clearance/dialysance of urea/other solute,
T—dialysis time,
V—volume of distribution of urea/solute, approximately equal to patient's total body water.

The calculation of dialysance or clearance for the given solute (e.g. urea) comprises, for example, the following steps, which rely on use of one parameter, namely the mass transfer coefficient, which is an expression of the performance characteristics of a dialyzer membrane.

In particular, in the case of purely diffusive mass transfer, dialysance or clearance may be expressed as a function of the solute mass transfer coefficient K0.A of the specific dialyzer. Mass transfer K0.A reflects solute diffusion in the dialysis membrane and fluid compartments, dependents on solute size and decreases when solute molecular weight increases. The term 'K0.A' matches with the asymptotic dialysance the dialyzer would deliver at infinite flow rates.

With the aim of calculating dialysance or clearance for the given solute (e.g. urea) different from lactate, the control unit derives first a mass transfer coefficient $(K0.A)_{lactate}$ for lactate of the membrane of the treatment unit.

For instance using the following formula, which is valid only in the case where no ultrafiltration occurs. This means $Q_F=0$ but also that internal phenomenon of filtration/backfiltration is not considered by this equation. In these conditions inlet and outlet flow rates are equal, namely $Qd_{in}=Qd_{out}$.

$$(K0.A)_{lactate} = K0.A = Qb \times \frac{\mathrm{Ln}\left(\frac{1-Z \times E}{1-E}\right)}{1-Z} \quad \text{Equation (4)}$$

With $E = \frac{D0}{Qb}$

With $Z = \frac{Qb}{Qd}$ and $NT = \frac{K0 \times A}{Qb}$

Note that in the above formula the value of dialysance at zero ultrafiltration is used. In case the value of dialysance (in this case lactate dialysance) at zero ultrafiltration ($Q_F=0$) is not available then there are at least two ways to estimate dialysance D0 at zero ultrafiltration as a function of a dialysance value D obtained at non-zero filtration.

$$D = D0 + \frac{QF}{2} \xrightarrow{yields} D0 = D - \frac{QF}{2} \quad \text{Equation (5)}$$

or $$D = D0 \times \left(1 - \frac{QF}{Qb_{in}}\right) + QF \xrightarrow{yields} D0 = Qb_{in} \times \frac{D-QF}{Qb_{in}-QF} \quad \text{Equation (6)}$$

Thus, in case a dialysance value D is available at non-zero ultrafiltration, above equations allows for estimating the dialysance at zero ultrafiltration D0 (step 301 in FIG. 6).

K0.A value (in particular $(K0.A)_{lactate}$) may then be derived from this D0 estimate using Equation 4 (step 302).

Then, based on $(K0.A)_{lactate}$ the (K0.A) value for a different solute may be calculated (step 303). As already mentioned mass transfer coefficient reflects solute diffusion in the dialysis membrane and fluid compartments, it is strongly dependent on solute size and decreases when solute molecular weight increases. Experimental data indicate that K0 (or K0.A) interpolation as a function of solute molecular weight is a power law:

$$K0.A = A.mw^{-b} = K0.A_{ref} \times \left(\frac{mw_{ref}}{mw}\right)^b \quad \text{Equation (7)}$$

Where 'ref' is a reference solute for which K0.A value is available.

Above interpolation law may be valid in a reasonably wide molecular weight range, e.g. 50 to 5000 g/mole. Urea will be often taken as reference solute, being commonly monitored and representative of the smallest solutes (mw 60 g/mole). Power law coefficient 'b' may be computed as soon as K0.A is available for two solutes of different molecular weight. In general coefficient 'b' depends upon the properties of the membrane 5 of the treatment unit 2: the manufacture of the treatment unit generally provides data sheets with in vitro or in vivo clearance/dialysance values over a relevant range of molecular weight solutes (>1000 g/mole), which may be used to compute 'b'.

For instance the following table provides reference values of K0.A for an exemplary plausible membrane used in dialysis, and which may then be used for calculating coefficient 'b' and then for extrapolating lactate to urea data from equation 7.

| Solute | Urea | Vitamin B12 | Lactate |
|---|---|---|---|
| mw (g/mole) | 60 | 1335 | 89 |
| K0.A (ml/min) | 720 | 200 | — |
| Power law coefficient | | b = 0.41 | — |

Once the (K0.A) for a solute different from lactate has been calculated, then dialysance for said different solute may be estimated for instance using the following equation (step 304 in FIG. 6):

$$D = \frac{Qb_{in} \times Qd_{in} - f \times (Qb_{in} - QF) \times (Qd_{in} + QF)}{Qd_{in} - f \times (Qb_{in} - QF)} \quad \text{Equation (8)}$$

-continued

With $$f = \left(\frac{Qb_{in} - QF}{Qb_{in}} \times \frac{Qd_{in} + QF}{Qd_{in}}\right)^{1/\gamma}$$

$$\gamma = \exp\left(\frac{QF}{K0.A}\right) \quad 1$$

where $Qb_{in}$=value of the blood flow rate at the inlet of the treatment unit (this value is typically known as it is either set by the user or estimated with known methods e.g. by measuring the angular speed of the blood pump and the pressure regimen in the blood line), $Qd_{in}$=value of the flow rate of fresh treatment liquid in the preparation line 19, QF=value of the ultrafiltration flow rate.

Alternatively, once the (K0.A) for a different solute has been calculated, then dialysance may be calculated for using equation 4 (to determine dialysance at zero ultrafiltration for said given solute) and then one of equations 5 or 6 to determine dialysance at non-zero ultrafiltration for the given solute. Equation 8 may alternatively be used for computing $(K0.A)_{lactate}$.

In summary, the control unit 10, by applying the above equations, is configured to calculate the dialysance for a given solute different from lactate from:

the calculated value of the dialysance for lactate, one or more of values of: the flow rate $Qd_{in}$ of fresh treatment liquid, the flow rate $Qd_{out}$ of spent dialysate liquid, the ultrafiltration flow rate $Q_F$ through the semipermeable membrane;

the blood flow rate Qb or the plasma flow rate Qp (in particular the measured or estimated values of these flow rates at the inlet of the treatment unit);

one or more established relationships (e.g., known ratios) between the value of the mass transfer coefficient $(K0.A)_{lactate}$ for lactate to the value of the mass transfer coefficient $(K0.A)_{solute}$ for the given solute.

It should be noted that the equations reported in previous section implicitly assume that blood and treatment fluid is 'one-phase' for the given solute. This 'one phase' model, using Qbin, provides results which although quite accurate represent a first approximation compared to reality. A more accurate model may consider that:

solutes may not be evenly distributed between plasma and red blood cells (RBCs), solutes transfer across RBC membrane may be 'slow'.

According to one further aspect of the invention, depending upon the solute, instead of blood flow $Qb_{in}$, equations 6 and 8 above may use plasma flow rate $Qp_{in}$ at the inlet of the blood treatment unit ($Qp_{in}=Qb_{in}*(1-Hct)$). Analogously, $Qp_{in}$ may be used in equation 4 for determining the K0.A value.

In particular, equations 4 and 6 may be used with $Qp_{in}$ instead of $Qp_{in}$, in order to arrive at the $(K0.A)_{lactate}$ for lactate. Then, equation 7 may be used for the calculation of the K0.A value for another solute. If for instance this other solute is urea it may be reasonably assumed that no concentration gradient is present between plasma and RBCs for urea, and thus transfer through the RBC membrane is sufficiently fast with respect to the blood dwell time in the dialyzer. In such case equation 8 for the calculation of urea dialysance D may be used selecting whole blood flow rate $Qb_{in}$. Instead, if dialysance of creatinine needs to be calculated, one should consider that creatinine mass transfer through RBC membrane is slow with respect to the blood dwell time in the dialyzer; consequently creatinine inside RBCs is more or less unchanged at dialyzer outlet. Thus, once K0.A is available for creatinine (e.g. via equation 7), dialysance for creatinine may be calculated with equation 8 using $Qp_{in}$ instead of $Qb_{in}$.

In summary, again referring to FIG. 6, the control unit is configured to calculate the dialysance for the given solute by:

measuring or calculating the value of dialysance for lactate at zero ultrafiltration (step 301), deriving a mass transfer coefficient $(K0.A)_{Lactate}$ for lactate of the membrane of the treatment unit (step 302) from:

the calculated value of the dialysance for lactate at zero ultrafiltration, one or more of values of: the flow rate $Qd_{in}$ of fresh treatment liquid, the flow rate $Qd_{out}$ of spent dialysate liquid, the ultrafiltration flow rate $Q_F$ through the semipermeable membrane, the blood flow rate Qb or the plasma flow rate Qp (in particular the measured or estimated values of these flow rates at the inlet of the treatment unit); Then the control unit derives the mass transfer coefficient $(K0.A)_{solute}$ for a given solute different from lactate (step 303) relying on one or more established ratios between the value of the mass transfer coefficient $(K0.A)_{lactate}$ for lactate to the value of the mass transfer coefficient $(K0.A)_{solute}$ for the given solute. Subsequently, the control unit calculates the dialysance for the given solute different from lactate (step 304) based on either equation 4 and one of equations 5 or 6 (which imply to first calculate dialysance at zero ultrafiltration), or using equation 8 (which allow direct calculation of the dialysance at non zero ultrafiltration) using Qbin or Qpin depending upon the transfer behavior of the selected solute.

In other words, once the mass transfer coefficient for the given solute has been determined, dialysance may be calculated based on:

the derived mass transfer coefficient for the given solute $(K0.A)_{solute}$; and one or more of values of: the flow rate $Qd_{in}$ of fresh treatment liquid, the flow rate $Qd_{out}$ of spent dialysate liquid, the ultrafiltration flow rate $Q_F$ through the semipermeable membrane, the blood flow rate Qb or the plasma flow rate Qp (in particular the measured or estimated values of these flow rates at the inlet of the treatment unit).

In accordance with another aspect, the parameter indicative of the effectiveness of the extracorporeal blood treatment based is the lactate dialysis dose $(KT)_{lactate}$ delivered over a reference time period T and the control unit may be configured to calculate (step 203 in FIG. 5), in addition to dialysance, also the lactate dialysis dose $(KT)_{lactate}$. If the time period is the total treatment time Tt during which a patient is submitted to extracorporeal blood treatment the total lactate dialysis dose for lactate is indicated as $(KTt)_{lactate}$.

The lactate dialysis dose $(KT)_{lactate}$ delivered over a reference time period T (or the total lactate dialysis dose for lactate $(KTt)_{lactate}$ delivered over the whole treatment time) may be determined in various ways.

A first procedure may be applied if the flow rates (namely blood flow rate Qb, fresh treatment liquid flow rate $Qd_{in}$, used treatment liquid flow rate $Qd_{out}$ and, if present, ultrafiltration flow rate $Q_F$) remain constant during the whole treatment time Tt or at least during a reference time period T which may be a fraction of the whole treatment time.

According to this first procedure, the control unit (10) may be configured to calculate lactate dialysis dose $(KT)_{lactate}$ or $(KTt)_{lactate}$ by:

determining the total effluent volume flown in the spent dialysate line EV in the course of the reference time period T or Tt, measuring the lactate concentration of said total effluent volume, calculating KT or KTt for lactate based on the lactate concentration in blood, lactate concentration in the fresh treatment liquid and lactate concentration in said effluent volume using the following formula $$(KT)_{lactate} = EV^* ((Cd_{in} - Cd_{out})/(Cd_{in} - Cb_{in}))  \quad \text{Equation (9)}$$

or $$(KTt)_{Lactate} = EV^* ((Cd_{in} - Cd_{out})/(Cd_{in} - Cb_{in}))  \quad \text{Equation (10)}$$

where

EV: effluent volume during T or Tt respectively, $Cd_{out}$ is the lactate concentration of the used treatment liquid;

$Cd_{in}$ is the lactate concentration of the fresh treatment liquid;

$Cb_{in}$ is the concentration of lactate in blood or in a blood component (plasma).

In case during a total treatment time Tt the flow rates (namely blood flow rate Qb, fresh treatment liquid flow rate $Qd_{in}$, used treatment liquid flow rate $Qd_{out}$ and, if present, ultrafiltration flow rate $Q_F$) remain constant at respective values during corresponding consecutive reference time periods Ti (each Ti being fraction of the whole treatment time), then the total dialysis dose for lactate $KTt_{lactate}$ may be calculated using the above process, namely equation 9, for each reference time period Ti and then making the sum of each 'partial' dialysis dose $(KT)i_{lactate}$ calculated for each reference time period Ti:

In other words, for each time period Ti equation 9 becomes:

$$(KT)i_{lactate} = EVi^* ((Cd_{in} - Cd_{out})/(Cd_{in} - Cb_{in}))$$

where

EVi: effluent volume collected during each respective time interval (Ti), $Cd_{out}$ is the lactate concentration of the used treatment liquid during each respective time interval (Ti), $Cd_{in}$ is the lactate concentration of the fresh treatment liquid during each respective time interval (Ti), $Cb_{in}$ is the concentration of lactate in blood or in a blood component (plasma) during each respective time interval (Ti).

The total dialysis dose for lactate $(KTt)_{lactate}$ is then determined making the sum of each partial dialysis dose for lactate $(KT)i_{lactate}$ for each reference time period Ti as follows:

$$(KTt)_{Lactate} = \Sigma (KT)i_{lactate}  \quad \text{Equation (11)}$$

The above procedure requires that the spent dialysate line is connected to a collection container where the entire spent dialysate volume is collected or to a collection container connected with a sampling line configured for regularly, e.g., periodically, sampling representative samples of the spent dialysate over the whole treatment time or over the reference time period. Moreover, the concentration of lactate in the liquid present in the collection container (such as container 23 or container 14) at the end of the treatment may need to be measured.

In the case where no representative sample(s) of the spent dialysate over the whole treatment (or over a reference time period of interest) is available, and/or flow rate changes have occurred one or more times along the treatment (or reference time period of interest), then the present invention provides for a second alternative procedure to calculate the total lactate dialysis dose $(KTt)_{Lactate}$ over treatment time Tt. In these conditions overall lactate $(KTt)_{lactate}$ may be estimated by making a sum of a plurality of lactate dialysis dose contributes (in a way similar to equation 11):

$$(KTt)_{lactate} = \Sigma (KT)i_{lactate} = \Sigma (Di_{lactate} \cdot Ti)  \quad \text{Equation (12)}$$

In greater detail, according to a second procedure, the control unit (10) may be configured to calculate lactate dialysis dose $(KT)_{lactate}$ by:

determining lactate dialysance for a first time period (T1) during which the blood flow rate (Qb), the flow rate $(Qd_{in})$ of fresh treatment liquid, and optionally ultrafiltration flow rate $(Q_F)$, are kept constant at first respective values;

calculating a lactate dose for the first time period multiplying the duration of the first time period times the lactate dialysance determined for the same first time period;

determining lactate dialysance for any further time period (Ti) during which the blood flow rate (Qb), the flow rate $(Qd_{in})$ of fresh treatment liquid, and optionally ultrafiltration flow rate $(Q_F)$, are kept constant at further respective values;

calculating a lactate dialysis dose for each one of said further time periods multiplying the duration of each further time period times the respective lactate dialysance determined for the same further time period;

summing the calculated lactate doses for the first time period and for each further time period to obtain the total lactate dose for the reference period (which may be total treatment time Tt) covering the first time period and any further time period using equation 12.

Finally, the invention provides for a third procedure in case where:

no representative sample(s) of the spent dialysate over the whole treatment (or over a reference time period of interest) is available, flow rate changes have occurred one or more times along the treatment (or reference time period of interest), spent dialysate lactate concentration is only measured once during the treatment (or during the reference time period of interest).

Under these circumstances and according to further aspects of the invention, the control unit may be configured to calculate dialysance for lactate at any given flow rate condition and consequently determine the overall lactate dose $(KT)_{lactate}$ or $(Kit)_{lactate}$ from the single lactate measurement, via the computation of lactate K0.A. If, for instance, we assume to have spent dialysate lactate concentration measured during a first time period (together with the values of all needed flow rates which remain constant during the first time period namely blood flow rate $(Qb)_1$, fresh treatment liquid flow rate $(Qd_{in})_1$ or used treatment liquid flow rate $(Qd_{out})_1$ and, if present, ultrafiltration flow rate $(Q_F)_1$, then lactate dialysance $(D1)_{lactate}$ for said first time period may be determined using above equation 2. Consequently, the control unit may be configured to determine the value of the lactate dialysance for a second time period $(D2)_{lactate}$ (and in general for any further time period) at which different, but known, flow rate conditions exist based on:

the value of dialysance $(D1)_{Lactate}$ for the first time period;

the values of blood flow rate $(Qb)_2$, fresh treatment liquid flow rate $(Qd_{in})_2$ or used treatment liquid flow rate $(Qd_{out})_2$ and, if present, ultrafiltration flow rate $(Q_F)_2$ at the second (or further) time period.

In practice, the control unit may be configured to calculate the value of dialysance $(D1)_{lactate}$ for the first time period (relying on equation 2 and using blood flow rate $(Qb)_1$, fresh treatment liquid flow rate $(Qd_{in})_1$ or used treatment liquid flow rate $(Qd_{out})_1$ and, if present, ultrafiltration flow rate $Q_{F1}$); then the control unit may calculate the mass transfer coefficient for lactate $(K0.A)_{lactate}$ using equation 4 and one of equations 5 or 6. Then—based on the $(K0.A)_{lactate}$ and the values of blood flow rate $(Qb)_2$, fresh treatment liquid flow rate $(Qd_{in})_2$ or used treatment liquid flow rate $(Qd_{out})_2$ and, if present, ultrafiltration flow rate $(Q_F)_2$ at the second (or further) time period—the control unit is configured to calculate dialysance for a second time period $(D2)_{lactate}$ using equation 4 and one of equations 5 or 6 (step represented by block 206 in FIG. 5). Note that, instead of equation 4, equation 8 may be used for the above calculations.

Once the dialysance values for the second and any further time periods have been calculated, each dialysance value is multiplied times the respective time period thereby calculating a lactate dialysis dose for each one of said time periods; then by making the sum of the calculated lactate doses for the first time period and for each further time period (see block 203 in FIG. 5), the control unit obtains the total lactate dose for the reference period (which may be total treatment time Tt) covering the first time period and any further time period (equation 12):

$$(KTt)_{actate} = \Sigma(K\ T)i_{lactate} = \Sigma(Di_{lactate} \cdot Ti)$$

The control unit may thus be configured to calculate the dialysis dose for the entire treatment time with knowledge of the dialysance value obtained with a single measure of spent dialysate lactate concentration, as long as there is knowledge of the flow rates (blood flow rate $Qb_{1...n}$, fresh treatment liquid flow rate $Qd_{in1...n}$ or used treatment liquid flow rate $Qd_{out1...n}$ and, if present, ultrafiltration flow rate $Q_{F1...n}$) of the time periods during which said flow rates apply.

Finally, in accordance with a further aspect the control unit may configured to periodically calculate the value of the parameter indicative of effectiveness (e.g., either dialysance D and/or dialysis dose KT for instance using the procedures and equations presented above) or the control unit may calculate said parameter value upon receiving an order form the user (e.g., via user interface) or the control unit may automatically trigger a new computation of the value of said parameter (D, KT) indicative of the effectiveness of the extracorporeal blood treatment every time the control unit receives an indication that there has been a change (for instance a new setting entered by a user via user interface) or detects a change (for instance a detection of a change in a real value) in one or more of following flow rates: blood flow rate $(Qb)$, fresh treatment liquid flow rate $(Qd_{in})$, used treatment liquid flow rate $(Qd_{out})$ and, if present, ultrafiltration flow rate $(Q_F)$.

EXAMPLES

1. Calculation of Lactate Dialysance at Constant Blood Flow Rate, Fresh Treatment Liquid Flow Rate and Ultrafiltration Flow Rate Blood flow:

$$Qb = Qb_{in} = 320\ \text{ml/min}$$

Fresh treatment liquid flow rate:

$$Qd = Qd_{in} = 500\ \text{ml/min}$$

Ultrafiltration flow rate:

$$Q_F = 15\ \text{ml/min}$$

Lactate concentration lactate in fresh treatment liquid:

$$Cd_{in} = 40.0\ \text{mmol/L}$$

Patient hematocrit:

$$Hct = 33\%$$

Lactate concentration in spent treatment liquid:

$$Cd_{out} = 25.8\ \text{mmol/L}$$

Plasma flow rate:

$$Qp = 320 \times (1-0.33) = 214.4\ \text{ml/min}$$

Patient plasma lactate estimate:

$$Cb_{in} = 4\ \text{mmol/L}$$

Lactate dialysance estimate using Equation 2:

$$D = (500 \times 40 - 515 \times 25.8)/(40-4) = 186.5\ \text{ml/min}$$

2. Calculation of Urea Dialysance at Constant Blood Flow Rate, Fresh Treatment Liquid Flow Rate and Ultrafiltration Flow Rate The same assumptions of example 1 apply.

After calculation of lactate dialysance with equation 2, then dialysance at zero ultrafiltration may be estimated with equation 5 or 6.

Subsequently, using equation 4, the mass transfer coefficient $(K0.A)_{lactate}$ for lactate is determined, which is $(K0.A)_{Lactate} = 547$ ml/min.

Afterwards, using equation 7 (which requires the knowledge of the value of the mass transfer coefficient (K0.A) for two solutes), the value of the mass transfer coefficient $(K0.A)_{solute}$ for the given solute (in this case urea) may be calculated, which is $(K0.A)_{solute} = 647$ ml/min.

Finally, using equation 8, it is possible to determine urea dialysance $D_{urea} = 239.5$ ml/min 3. Calculation of Dialysance and of Dialysis Dose Based on Knowledge of Dialysance at First Values of Blood Flow Rate, Fresh Treatment Liquid Flow Rate and Ultrafiltration Flow Rate This example shows:

calculation of dialysance at first flow rate conditions defined by known values blood flow rate $Qb_1$, fresh treatment liquid flow rate $Qd_{in1}$ or used treatment liquid flow rate $Qd_{out1}$ and ultrafiltration flow rate $Q_{F1}$ which are stable for a first time period; the calculation is made relying on equation 1 and using a measured value of $Cd_{out1}$ taken during the first time period;

calculation of dialysance at second flow rate conditions of blood flow rate $Qb_2$, fresh treatment liquid flow rate $Qd_{in2}$ or used treatment liquid flow rate $Qd_{out2}$ and ultrafiltration flow rate $Q_{F2}$, which are stable for a second time period consecutive to the first time period;

calculation of KT for the first and second time periods; calculation of total treatment time KT.

First Time Period Conditions

Blood flow:

$Qb=Qb_{in}=320$ ml/min

Fresh treatment liquid flow rate:

$Qd=Qd_{in}=500$ ml/min

Ultrafiltration flow rate:

$Q_F=15$ ml/min

Concentration of lactate in fresh treatment liquid:

$Cd_{in}=40.0$ mmol/L

Patient hematocrit:

$Hct=33\%$

Lactate concentration in spent treatment liquid:

$Cd_{out}=25.8$ mmol/L

Plasma flow rate:

$Qp=320\times(1-0.33)=214.4$ ml/min

Patient plasma lactate estimate:

$Cb_{in}=4$ mmol/L

Second Time Period Conditions (Change of Blood Flow Rate)

Blood flow:

$Qb=Qb_{in}=260$ ml/min

Fresh treatment liquid flow rate:

$Qd=Qd_{in}=500$ ml/min

Ultrafiltration flow rate:

$Q_F=15$ ml/min

Concentration of lactate in fresh treatment liquid:

$Cd_{in}=40.0$ mmol/L

Patient hematocrit:

$Hct=33\%$

Lactate concentration in spent treatment liquid:

$Cd_{out}=$ not known

Plasma flow rate:

$Qp=260\times(1-0.33)=174.2$ ml/min

Patient plasma lactate estimate:

$Cb_{in}=4$ mmol/L

| Period | Time Period 1 | Time Period 2 | Overall treatment |
|---|---|---|---|
| Time | 2 h 30 | 1 h 30 | 4 h 00 |
| Qd, $Q_F$, Hct, $Cd_{in}$ | | Same as §3.2 | |
| Qb | 320 ml/min | 260 ml/min | |
| Qp | 214 ml/min | 174 ml/min | |
| $D_{lactate}$ | 184.4 ml/min | 161.1 ml/min | |
| $K0.A_{lactate}$ | 565 ml/min | 547 ml/min | 547 ml/min |
| $K.T_{lactate}$ | 59.7 L | 41.9 L | 101.6 L |

Control unit

As already indicated the apparatus according to the invention makes use of at least one control unit. This control unit may comprise a digital processor (CPU) with memory (or memories), an analogical type circuit, or a combination of one or more digital processing units with one or more analogical processing circuits. In the present description and in the claims it is indicated that the control unit is "configured" or "programmed" to execute certain steps: this may be achieved in practice by any means which allow configuring or programming the control unit. For instance, in case of a control unit comprising one or more CPUs, one or more programs are stored in an appropriate memory: the program or programs containing instructions which, when executed by the control unit, cause the control unit to execute the steps described and/or claimed in connection with the control unit. Alternatively, if the control unit is of an analogical type, then the circuitry of the control unit is designed to include circuitry configured, in use, to process electric signals such as to execute the control unit steps herein disclosed.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and the scope of the appended claims.

The invention claimed is:

1. An apparatus for extracorporeal treatment of blood comprising:
    a preparation line having one end configured for being connected to an inlet of a secondary chamber of a treatment unit, a semi-permeable membrane separating said secondary chamber from a primary chamber of the same treatment unit;
    a spent dialysate line having one end configured for being connected to an outlet of said secondary chamber; and
    a control unit configured for commanding execution of the following steps:
        causing a fresh treatment liquid to flow in the preparation line towards the secondary chamber at a flow rate, the treatment liquid including lactate;
        causing a used treatment liquid to flow in the spent dialysate line at a flow rate;
        receiving one or more measured values of a parameter related to the concentration of lactate in the used treatment liquid flowing in the spent dialysate line; and
        computing at least one value of a parameter indicative of the effectiveness of the extracorporeal blood treatment based on:
            said one or more measured values of the parameter related to the concentration of lactate of the used treatment liquid; and
            at least one of: said flow rate of fresh treatment liquid and said flow rate of used treatment liquid.

2. The apparatus according to claim 1, wherein the control unit is further configured for receiving one or more values of a parameter related to the concentration of lactate of the fresh treatment liquid flowing in the preparation line.

3. The apparatus according to claim 2, wherein the step of receiving one or more values of a parameter related to the concentration of lactate of the fresh treatment liquid flowing in the preparation line includes one of:
    measuring one or more actual values of the parameter related to the concentration of lactate of the fresh treatment liquid flowing in the preparation line,
    retrieving from a memory one or more preset values of the parameter related to the concentration of lactate of the fresh treatment liquid flowing in the preparation line, or receiving from a user interface one or more input values of the parameter related to the concentration of lactate of the fresh treatment liquid flowing in the preparation line.

4. The apparatus according to claim 2, wherein computing at least one value of a parameter indicative of the effectiveness of the extracorporeal blood treatment is based on:
said one or more measured values of the parameter related to the concentration of lactate of the used treatment liquid;
said one or more values of the parameter related to the concentration of lactate of the fresh treatment liquid; and
at least one of: said flow rate of fresh treatment liquid or said flow rate of used treatment liquid.

5. The apparatus according to claim 4, wherein the step of causing a fresh treatment liquid to flow in the preparation line comprises the sub-step of maintaining, at least for a time interval, the concentration of the lactate in the fresh treatment liquid constant at a set value which represents the value of the parameter related to the concentration of lactate of the fresh treatment liquid used for computing the at least one value of a parameter indicative of the effectiveness of the extracorporeal blood treatment.

6. The apparatus according to claim 5, wherein said one or more measured values of the parameter related to the concentration of lactate in the used treatment liquid are representative of measures of the parameter related to the concentration of lactate taken during one of:
said time interval, or
a further time interval delayed by a hydraulic delay with respect to said time interval.

7. The apparatus according to claim 1, wherein the control unit is further configured for:
receiving a total treatment time, which is a time during which the apparatus operates with blood in the extracorporeal circuit and a patient connected to the extracorporeal circuit;
maintaining the concentration of the lactate in the fresh treatment liquid constant at said set value during a time interval lasting for a significant portion of the treatment time; and
calculating a plurality of consecutive times during said time interval the value of the parameter indicative of the effectiveness of the extracorporeal blood treatment,
wherein said significant portion of the treatment time comprising a portion of time is selected from the group consisting of:
at least 10% of said total treatment time (Tt),
at least 30% of said total treatment time (Tt),
at least 70% of said total treatment time (Tt), and
the entire treatment total time (Tt).

8. The apparatus according to claim 1, further comprising:
an outlet lactate concentration sensor connected to the control unit, the outlet lactate concentration sensor being operative at one of:
said spent dialysate line,
a line connected to the spent dialysate line, or
a line connected to the outlet of said secondary chamber,
wherein the outlet lactate concentration sensor is configured for measuring one or more real values of the lactate concentration lactate in the fluid exiting from the secondary chamber, and
wherein the control unit is configured to receive, a measured value or values of the parameter related to the concentration of lactate in the used treatment liquid, the one or more measured real values of the lactate concentration detected by the outlet lactate concentration sensor.

9. The apparatus according to claim 1, wherein the apparatus includes at least a blood pump configured to operate on an extracorporeal blood circuit connectable to the primary chamber of said blood treatment unit, said control unit being connected to the blood pump and being configured to:
operate the blood pump to cause flow of a patient's blood in the extracorporeal blood circuit at a blood flow rate,
receive or store a value representative of the concentration of lactate in the patient's blood or in a blood component of the patient's blood,
and wherein the parameter indicative of the effectiveness of the extracorporeal blood treatment is calculated based on:
at least one measured value of the parameter related to the concentration of lactate in the used treatment liquid;
at least one measured value of the parameter related to the concentration of lactate in the fresh treatment liquid;
said flow rate of fresh treatment liquid; and
said value representative of the concentration of lactate in the patient's blood or in the blood component of the patient's blood.

10. The apparatus according to claim 6, wherein, at least during said time interval or during said further time interval, the control unit is configured to keep constant the flow rate of fresh treatment liquid in the preparation line, the flow rate of the patient's blood in the extracorporeal blood circuit, and the flow rate of ultrafiltration flow through the semipermeable membrane.

11. The apparatus according to claim 1, wherein the parameter indicative of the effectiveness of the extracorporeal blood treatment is lactate dialysance, which is calculated using the following formula:

$$D=(Qd\text{in}\times(Cd\text{in}-Cd\text{out})+QP\times Cd\text{out})/(Cd\text{in}-Cb\text{in})$$

where

D is the calculated value of dialysance for lactate, $Cd_{out}$ is the measured value of the parameter related to the concentration of lactate of the used treatment liquid, $Cd_{in}$ is measured value of the parameter related to the concentration of lactate of the fresh treatment liquid, $Qd_{in}$ is the flow rate of fresh treatment liquid;

$Cb_{in}$ is the value representative of the concentration of lactate in blood or in a blood component, and $Q_F$ is the value of ultrafiltration flow rate through the semipermeable membrane.

12. The apparatus according to claim 1, wherein the control unit is configured for causing the fresh treatment liquid to flow in the preparation line towards the secondary chamber at a constant lactate concentration, which is set at a set value comprised between 35 mmol/l and 45 mmol/l.

13. The apparatus according to claim 9, wherein the value representative of the concentration of lactate in blood or in a blood component is a known value selected in the range comprised between 1 and 5 mmol/l.

14. The apparatus according to claim 1, wherein the parameter indicative of the effectiveness of the extracorporeal blood treatment is lactate dialysance, and wherein the control unit is configured to calculate the dialysance for a given solute different from lactate using:
the calculated value of the lactate dialysance, and
one or more established relationships between the value of a mass transfer coefficient for lactate to the value of a mass transfer coefficient for the given solute, the mass transfer coefficient reflecting a solute diffusion through the membrane.

15. The apparatus according to claim 14, wherein the parameter indicative of the effectiveness of the extracorporeal blood treatment is lactate dialysance, and wherein the control unit is configured to calculate dialysance for a given solute different from lactate,
the calculation of dialysance for the given solute comprising:
deriving a mass transfer coefficient for lactate of the membrane of the treatment unit from the calculated value of the dialysance for lactate;
determining a mass transfer coefficient of the membrane of the treatment unit for the given solute based on the value of the mass transfer coefficient for lactate;
calculating the dialysance for the given solute based on the mass transfer coefficient for the given solute; and
wherein the lactate dialysance and the dialysance for the given solute different from lactate are calculated at same values of:
the flow rate of fresh treatment liquid,
the ultrafiltration flow rate through the semipermeable membrane, and
the blood flow rate in the extracorporeal circuit.

16. The apparatus according to claim 14, wherein the control unit is further configured for:
identifying the solute for which dialysance is to be calculated;
determining if a mass transfer time of the solute through red blood cells is greater, optionally at least 5 times greater, than a blood dwell time of blood flowing through the blood treatment unit; and
using the value of the plasma flow rate at the inlet of the blood treatment unit as an effective value of the blood flow rate for the purpose of calculating the solute mass transfer coefficient, if it has been determined that the mass transfer time of the solute through red blood cells is greater, optionally 5 times greater, than a blood dwell time in the blood treatment unit,
where $Qp_{in}=(1-Hct)*Qb_{in}$, and
with $Qp_{in}$ being the plasma flow rate at the inlet of the blood treatment unit, Hct being the hematocrit of the patient's blood in the arterial line at the inlet of the blood treatment unit, and $Qb_{in}$, being the blood flow rate at the inlet of the blood treatment unit.

17. The apparatus according to claim 14, wherein the mass transfer coefficient for lactate of the membrane of the treatment unit is derived by:
measuring or calculating the value of dialysance for lactate, in particular at zero ultrafiltration;
deriving a mass transfer coefficient for lactate of the membrane of the treatment unit from:
the calculated value of the dialysance for lactate, in particular at zero ultrafiltration,
one or more of values of: the flow rate of fresh treatment liquid, the flow rate of spent dialysate liquid, the ultrafiltration flow rate through the semipermeable membrane, and
the blood flow rate or the plasma flow rate, in particular one of the plasma flow rate at the inlet of the blood treatment unit and the blood flow rate at the inlet of the blood treatment unit;
wherein the mass transfer coefficient for the given solute is derived using one or more established relationships between the value of the mass transfer coefficient for lactate to the value of the mass transfer coefficient for the given solute; and
wherein the dialysance of the given solute is calculated based on:
one or more values of: the flow rate of fresh treatment liquid, the flow rate of spent dialysate liquid, the ultrafiltration flow rate through the semipermeable membrane,
one of the blood flow rate or the plasma flow rate, in particular one of the plasma flow rate at the inlet of the blood treatment unit and the blood flow rate at the inlet of the blood treatment unit, and
the determined mass transfer coefficient for the given solute.

18. The apparatus according to claim 17, wherein the step of deriving a mass transfer coefficient for lactate of the membrane of the treatment unit comprises:
measuring or calculating the value of dialysance for lactate at zero ultrafiltration, and
calculating the mass transfer coefficient for lactate of the membrane of the treatment unit using the calculated value of the dialysance for lactate at zero ultrafiltration,
wherein the step of calculating dialysance of the given solute comprises:
first determining the value of the dialysance for the given solute, at zero ultrafiltration, based upon:
the determined mass transfer coefficient for the given solute; and
one of:
the flow rate of fresh treatment liquid and the flow rate of spent dialysate liquid; or
one or the blood flow rate or the plasma flow rate, in particular one of the plasma flow rate at the inlet of the blood treatment unit and the blood flow rate at the inlet of the blood treatment unit; and
second determining dialysance for the given solute at non-zero ultrafiltration based upon:
the determined value of the dialysance for the given solute at zero ultrafiltration, and the value of the ultrafiltration flow rate; or
the determined value of the dialysance for the given solute at zero ultrafiltration, the value of the ultrafiltration flow rate through the semipermeable membrane, and one of the blood flow rate or plasma flow rate, in particular one of the plasma flow rate at the inlet of the blood treatment unit and the blood flow rate at the inlet of the blood treatment unit.

19. The apparatus according to claim 1, wherein the parameter indicative of the effectiveness of the extracorporeal blood treatment comprises a lactate dialysis dose delivered over a reference time period and
wherein the control unit is configured to calculate the lactate dialysis dose by:
determining the total effluent volume flow through the spent dialysate line in the course of the reference time period, and measuring the lactate concentration of said total effluent volume, or wherein the control unit is configured to calculate lactate dialysis dose by:

receiving said one or more values of a parameter related to the concentration of lactate of the fresh treatment liquid flowing in the preparation line measured during the reference time period, receiving values of the following flow rates, which remain constant during the time period: blood flow rate, one of fresh treatment liquid flow rate or used treatment liquid flow rate, and, if present, ultrafiltration flow rate, calculating a value of lactate dialysance for said time period, and calculating a lactate dialysis dose for said time period multiplying the duration of the time period times the lactate dialysance-determined for the same time period.

20. The apparatus according to claim 1, wherein the control unit is configured to automatically trigger a new computation of at least one value of said parameter indicative of the effectiveness of the extracorporeal blood treatment every time the control unit receives an indication that there has been a change or detects a change in one or more of: blood flow rate, fresh treatment liquid flow rate, used treatment liquid flow rate, and, if present, ultrafiltration flow rate.

* * * * *